US008484000B2

(12) United States Patent
Gulati

(10) Patent No.: US 8,484,000 B2
(45) Date of Patent: Jul. 9, 2013

(54) DETECTING EVENTS OF INTEREST USING QUANTUM RESONANCE INTERFEROMETRY

(75) Inventor: Sandeep Gulati, La Canada, CA (US)

(73) Assignee: ViaLogy LLC, Altadena, CA (US)

( * ) Notice: Subject to any disclaimer, the term of this patent is extended or adjusted under 35 U.S.C. 154(b) by 1848 days.

(21) Appl. No.: 11/219,521

(22) Filed: Sep. 2, 2005

(65) Prior Publication Data

US 2006/0053005 A1    Mar. 9, 2006

Related U.S. Application Data

(60) Provisional application No. 60/606,471, filed on Sep. 2, 2004.

(51) Int. Cl.
| G06G 7/48 | (2006.01) |
| G06G 7/50 | (2006.01) |
| G01N 33/48 | (2006.01) |
| G01N 33/50 | (2006.01) |
| G01N 3/00 | (2006.01) |
| G06F 19/00 | (2011.01) |
| G06F 19/10 | (2011.01) |

(52) U.S. Cl.
CPC ............... *G06F 19/00* (2013.01); *G06F 19/10* (2013.01)
USPC ............. 703/5; 703/3; 703/4; 702/19; 702/22

(58) Field of Classification Search
None
See application file for complete search history.

(56) References Cited

U.S. PATENT DOCUMENTS

| 3,786,341 | A | 1/1974 | Anderson et al. |
| 4,665,440 | A | 5/1987 | Tromborg |
| 4,686,695 | A | 8/1987 | Macovski |
| 5,134,528 | A | 7/1992 | Sato |
| 5,168,499 | A | 12/1992 | Peterson et al. |
| 5,236,826 | A | 8/1993 | Marshall |
| 5,389,512 | A | 2/1995 | Sninsky et al. |
| 5,442,593 | A | 8/1995 | Woodbury et al. |
| 5,445,934 | A | 8/1995 | Fodor et al. |
| 5,462,879 | A | 10/1995 | Bentsen |
| 5,492,840 | A | 2/1996 | Malmqvist et al. |
| 5,539,517 | A | 7/1996 | Cabib et al. |
| 5,552,270 | A | 9/1996 | Khrapko et al. |
| 5,561,071 | A | 10/1996 | Hollenberg et al. |
| 5,576,176 | A | 11/1996 | Adams et al. |
| 5,605,662 | A | 2/1997 | Heller et al. |
| 5,631,134 | A | 5/1997 | Cantor |
| 5,631,734 | A | 5/1997 | Stern et al. |
| 5,632,041 | A | 5/1997 | Peterson et al. |
| 5,679,510 | A | 10/1997 | Ray et al. |
| 5,683,881 | A | 11/1997 | Skiena |
| 5,688,648 | A | 11/1997 | Mathies et al. |
| 5,700,637 | A | 12/1997 | Southern |
| 5,733,729 | A | 3/1998 | Lipshutz |
| 5,741,644 | A | 4/1998 | Kambara et al. |
| 5,763,175 | A | 6/1998 | Brenner |
| 5,784,162 | A | 7/1998 | Cabib et al. |
| 5,817,462 | A | 10/1998 | Garini et al. |
| 5,825,936 | A | 10/1998 | Clarke et al. |
| 5,848,996 | A | 12/1998 | Eldor |
| 5,858,659 | A | 1/1999 | Sapolsky |
| 5,858,732 | A | 1/1999 | Solomon et al. |
| 5,863,764 | A | 1/1999 | Hillman et al. |
| 5,874,162 | A | 2/1999 | Bastian et al. |
| 5,874,214 | A | 2/1999 | Nova et al. |
| 5,885,578 | A | 3/1999 | Salk et al. |
| 5,925,525 | A | 7/1999 | Fodor |
| 5,968,740 | A | 10/1999 | Fodor |
| 5,974,164 | A | 10/1999 | Chee |
| 6,025,601 | A | 2/2000 | Trulson |
| 6,066,454 | A | 5/2000 | Lipshutz et al. |
| 6,088,099 | A | 7/2000 | Cabib et al. |
| 6,090,555 | A | 7/2000 | Fiekowsky et al. |
| 6,136,541 | A | 10/2000 | Gulati |
| 6,142,681 | A | 11/2000 | Gulati |
| 6,171,793 | B1 | 1/2001 | Phillips |
| 6,185,548 | B1 * | 2/2001 | Schwartz et al. ............... 706/21 |
| 6,185,561 | B1 | 2/2001 | Balaban et al. |
| 6,218,122 | B1 | 4/2001 | Friend et al. |
| 6,223,127 | B1 | 4/2001 | Berno |
| 6,225,625 | B1 | 5/2001 | Pirrung et al. |

(Continued)

FOREIGN PATENT DOCUMENTS

| EP | 0077149 | 1/1986 |
| EP | 0437829 | 10/1994 |

(Continued)

OTHER PUBLICATIONS

Jensen RV. Quantum Chaos. Nature, vol. 355, 1992, pp. 311-318.*
Absorption spectrum, 2006, two pages. Obtained online on Jul. 29, 2012 from <<http://www.credoreference.com/entry/collinsastron/absorption_spectrum>>.*
Alacid et al., "Bound and resonance states by a time-independent filter diagonalization method for large Hamiltonian systems," Chemical Physics Letters 305: 258-262 (1999).
Ando, B. and S. Graziani, *Stochastic Resonance: Theory and Applications*, Boston: Kluwer Academic Publishers, pp. 11-91 (2000).
Baez et al., "Irving Ezra Segal (1918-1998)," Notices of the American Mathematical Society 46(6): 659-668 (Jun./Jul. 1999).
Brockman, J., "Whole-Loan Traders Find Marketplace on Web Site," American Banker 163(36): 10 (Feb. 24, 1998).

(Continued)

*Primary Examiner* — Russell S Negin
(74) *Attorney, Agent, or Firm* — Fish & Richardson P.C.

(57) ABSTRACT

Incoming data from, for example, an array of detectors, may be received. A dynamical system may be initialized corresponding to a modality of the incoming data so that a measurement probe based on the initialized dynamical system may be generated. Such a measurement probe may be injected into a quantum mechanical system so that it may be determined whether the injection of the measurement probe into the quantum mechanical system results in a collapse of the quantum mechanical system. Thereafter, it may be determined that a signal is present within the incoming data if the quantum mechanical system collapses. Related methods, apparatuses, systems, and computer-program products are also described.

16 Claims, 12 Drawing Sheets

U.S. PATENT DOCUMENTS

| | | | |
|---|---|---|---|
| 6,228,593 | B1 | 5/2001 | Lipshutz et al. |
| 6,229,911 | B1 | 5/2001 | Balaban |
| 6,242,180 | B1 | 6/2001 | Chee |
| 6,245,511 | B1 | 6/2001 | Gulati |
| 6,294,327 | B1 | 9/2001 | Walton et al. |
| 6,308,170 | B1 | 10/2001 | Balaban |
| 6,342,355 | B1 | 1/2002 | Hacia |
| 6,344,316 | B1 | 2/2002 | Lockhart |
| 6,361,937 | B1 | 3/2002 | Stryer |
| 6,368,799 | B1 | 4/2002 | Chee |
| 6,370,478 | B1 | 4/2002 | Stoughton |
| 6,391,550 | B1 | 5/2002 | Lockhart |
| 6,420,108 | B2 | 7/2002 | Mack |
| 6,453,241 | B1 | 9/2002 | Bassett |
| 6,468,744 | B1 | 10/2002 | Cronin |
| 6,490,533 | B2 | 12/2002 | Weiner |
| 6,671,625 | B1 | 12/2003 | Gulati |
| 6,704,662 | B2 | 3/2004 | Gulati |
| 6,780,589 | B1 | 8/2004 | Gulati |
| 6,963,806 | B2 | 11/2005 | Gulati |
| 2003/0044775 | A1* | 3/2003 | Gulati ........................ 435/5 |
| 2003/0215867 | A1 | 11/2003 | Gulati |
| 2004/0064261 | A1 | 4/2004 | Gulati |
| 2004/0111219 | A1 | 6/2004 | Gulati |

FOREIGN PATENT DOCUMENTS

| | | |
|---|---|---|
| EP | 0426564 | 12/1994 |
| EP | 0854197 | 7/1998 |
| EP | 1026260 | 8/2000 |
| EP | 0802426 | 11/2001 |
| EP | 1406201 | 4/2004 |
| EP | 1145177 | 10/2004 |
| EP | 1145181 | 10/2004 |
| EP | 1157347 | 10/2004 |
| WO | 93/13711 | 7/1993 |
| WO | 93/21339 | 10/1993 |
| WO | 97/02488 | 1/1997 |
| WO | 98/07888 | 2/1998 |
| WO | 98/37417 | 8/1998 |
| WO | 98/48048 | 10/1998 |
| WO | 99/31275 | 6/1999 |
| WO | 99/39008 | 8/1999 |
| WO | 99/44063 | 9/1999 |
| WO | 99/45148 | 9/1999 |
| WO | 99/66024 | 12/1999 |
| WO | 00/05408 | 2/2000 |
| WO | 00/12759 | 3/2000 |
| WO | 00/28091 | 5/2000 |
| WO | 00/39339 | 7/2000 |
| WO | 00/51055 | 8/2000 |
| WO | 00/51056 | 8/2000 |
| WO | 00/52625 | 9/2000 |
| WO | 2004/102456 | 11/2004 |

OTHER PUBLICATIONS

Brody et al., "Geometry of Quantum Statistical Interference," Physical Review Letters 77(14): 2851-2855 (Sep. 30, 1999).

Brown, P.O. and D. Botstein, "Exploring the New World of the Genome with DNA Microarrays," Nature Genetics 21 (Suppl.): 33-37 (Jan. 1999).

Caldiera, A.O. and A.J. Leggett, "Quantum Tunnelling in a Dissipative System," Annals of Physics, 149: 374-456 (1983).

Chandre et al., "Kolmogorov-Arnold-Moser renormalization-group approach to the breakup of invariant tori in Hamiltonian systems," Physical Review E 57(2): 1536-1543 (Feb. 1998).

Daido, "Multibranch Entrainment and Scaling in Large Populations of Coupled Oscillators", Phys. Rev. Lett. 77: 1406-1409 (1996).

Dailey P.J. and D. Hayden, "Viral load assays: methodologies, variables, and interpretation," Chapter 13 in: Cohen PT, Sande MA, Volberding PA, eds. *The AIDS knowledge base: a textbook on HIV disease from the University of California, San Francisco, and San Francisco General Hospital*. 3d ed. San Francisco: HIV InSite, 1998 & also available at the: *The AIDS Knowledge Base* [online] (Apr. 1998), http://hivinsite.ucsf.edu/skb/current/02qrna/index.html> [retrieved on Oct. 5, 2000]].

Darling et al., "Adiabatic Analysis of Quantum Dynamics", Physical Review Letters, 78(9): 1731-1734 (Mar. 3, 1997).

Finkelstein, B., "Secondary market participants seek to do business on website," Origination News; 7(9): 100 (Jun. 1998).

Freeman, M., "Automated MBS Trading—A First at First Boson," Wall Street & Technology 11(13): 10 (May 1994).

Gammaitoni et al., "Extraction of Periodic Signals from a Noise Background", Physics Letters A, 142(2-3): 59-62 (Dec. 4, 1989).

Gammaitoni et al., "Stochastic Resonance", Review of Modem Physics, 70(1): 223-287 (Jan. 1998).

Gardner, William, A. (Ed.), *Cyclostationarity in Communications and Signal Processing*, New York: IEEE Press, pp. 46-47 (1994).

GeneChip produced by Affymetrix, http://www/affymetrix.com/products/arrays/index.affx, 1 page, (accessed on Dec. 12, 2005).

Gonima, L., "Simple algorithm for the atmospheric correction of reflectance images," International Journal of Remote Sensing 14(6): 1179-1187 (1993).

Goychuk, I. and P. Hänggi, "Quantum Stochastic Resonance in Parallel", New Journal of Physics, 1: 14.1-14.14 (Aug. 27, 1999).

Grifoni et al., "Dissipation, Decoherence and Preparation Effects in the Spin-Boson System," The European. Phys. J. B 10: 719-729 (Feb. 1999).

Ter Haar, D., "The Canonical Equations of Motion," Chapter 5 in *Elements of Hamiltonian Mechanics*, Amsterdam: North-Holland Publishing Company, pp. 95-103 (1961).

Harris, F. and D.S. King, "Adaptive filters using fractal dimension of data," Proceedings of the Asilomar Conference on Signals, Systems, and Computers, New York: IEEE, 24: 278-282 (Nov. 5, 1990).

Heller et al., "Discovery and analysis of inflammatory disease-related genes using cDNA microarrays," Proceedings of the National Academy of Sciences (USA), 94: 2150-2155 (Mar. 1997).

Imafuku et al., "Quantum Stochastic Resonance in Driven Spin-Boson System with Stochastic Limit Approximation," arXiv:quant-ph/9910025 1: 1-9 (Oct. 6, 1999).

Jordan et al., "The Variational Formulation of the Fokker-Planck Equation," Siam. J. Math. Anal., 29(1): 1-17 (Jan. 1998).

Keegan, J., "Big Pension Funds Like Calpers Get Comfy with Private Equity," Investment Dealers' Digest-IDD pp. 13 (Aug. 24, 1998).

Kilin et al., "Complex Quantum Structure of Nonclassical Superposition States and Quantum Instability in Resonance Fluorescence," Physical Review Letters 76(7): 1051-1054 (1996).

Knight, A., "Whole loans on the Net," Wall Street & Technology 16(1):74 (Jan. 1998).

Leggett et al., "Dynamics of the Dissipative Two-State System," Reviews of Modern Physics 59(1): 1-85 (Jan. 1987).

Lemm et al., "A Bayesian Approach to Inverse Quantum Statistics", Physics Review Letters, 84(10): 2068-2071, (Mar. 6, 2000).

Lew, R.R. and C.L. Schauf, "Fractal Filtering of Channel Data," Biochim Biophys ACTA 1023(2): 305-311 (1990).

Li, C. and W.H. Wong et al., "Model-Based Analysis of Oligonucleotide Arrays: Expression Index Computation and Outlier Detection," Proc. Natl. Acad. Sci. USA 98(1): 31-36 (Jan. 2, 2001).

Lin et al., "A porous silicon-based optical interferometric biosensor," Science 278: 840-843 (1997).

Lindner et al., "Array enhanced stochastic resonance and spatiotemporal synchronization," Physical Review Letters 75(1): 3-6 (Jul. 3, 1995).

Löcher et al., "Spatiotemporal Stochastic Resonance in a System of Coupled Diode Resonators", Physical Review Letters, 77(23): 4698-4701 (Dec. 2, 1996).

Lofstedt, R. and S.N. Coppersmith, "Quantum Stochastic Resonance," Phys Rev. Letters, 72(13): 1947-1950 (1994).

Makarov, D.E. and N. Makri, "Stochastic resonance and nonlinear response in double-quantum-well structures," Physical Review B 52(4): R2257-R2260 (Jul. 15, 1995).

Maybeck, P.S., "Introduction," Chapter 1 in *Stochastic Models, Estimation, and Control*, vol. 1, New York: Academic Press, pp. 1-16 (1979).

McNamara, B. and K. Wisenfeld, "Theory of Stochastic Resonance," Phys Rev. A 39: 4854-4869 (May 1, 1989).

Merigan, T., "Individualization of therapy using viral markers," Journal of Acquired Immune Deficiency Syndromes and Human Retrovirology 10(Suppl 1): S41-S46 (1995).

Mitaim et al., "Adaptive Stochastic Resonance," Proceedings of the IEEE 86(11): 2152-2183 (Nov. 1998).

Nishiyama, "Numerical Analysis of the Dissipative Two-State System with the Density-Matrix Hilbert-space-reduction Algorithm," The European Physical Journal B, 12:547-554, (1999).

Pathria, R.K., "The Theory of Simple Gases," Chapter 6 in *Statistical Mechanics*, Toronto: Pergamon Press, pp. 136-147 (1972).

Setala, J., "The Future of Ag Lending Part III: Ag Lender Perspectives," Agri Finance 2(4): 1, 6-9 (Apr. 1998).

Simonotto et al., "Visual Perception of Stochastic Resonance", Phys Rev. Lett. 78: 1186-1189 (Feb. 10, 1997).

Sinnock, B., "MBS Trade Slows As Benchmark Bond Yields Spread Prepays Fears," National Mortgage News 22(13): 6 (Dec. 1997).

Somaroo et al., "Expressing the Operations of Quantum Computing in Multiparticle Geometric Algebra", Phys. Lett. A 240: 1-7 (Mar. 23, 1998).

Stinchcombe, R.B. and G.M. Schütz, "Application of Operator Algebras to Stochastic Dynamics and the Heisenberg Chain", Physical Review Letters, 75(1): 140-143 (Jul. 3, 1995).

Tsaur, G. and J. Wang, "Energy diffusion due to non-linear perturbation on linear Hamiltonians," Physical Review E. 54(5): 4657-4666 (1996).

Van Leeuwen, R., "Causality and Symmetry in Time-Dependent Density-Functional Theory", Physical Review Letters, 80(6): 1280-1283 (Feb. 9, 1998).

Vitali, D. and R. Mannella, "Quantum Stochastic Resonance in the Dissipative Two-State Systems," Il Nuovo Cimento della societá italianian di fisica 17D(7-8):959-967 (Jul. 1995).

Wells, D.A., "Hamilton's Equations of Motion," Chapter 16 in *Theory and Problems of Lagrangian Dynamics with a treatment of Euler's Equations of Motion, Hamilton's Equations and Hamilton's Principles*, Schaum's Outline Series, New York: McGraw-Hill Company, pp. 316-321 (1967).

Wornell et al., "Estimation of Fractal Signals from Noisy Measurements Using Wavelets," IEEE Transactions on Signal Processing 40(3): 611-623 (Mar. 1992).

Saha, "Fast estimation of transverse fields in high-finesse optical cavities" (J. Opt. Soc, Am. A, vol. 14, (1997) pp. 2195-2202).

Pfeifer et al., "The Virtual Interferometer—A tool for the systematic assessment of error-sources in interferometry", (CIRP Annals-Manufacturing Technology, vol. 51 (2002) pp. 455-458).

Vol'pov et al., "Active interferometric method for construction of images of small objects observed across a turbulent atmosphere," Soviet Journal of Quantum Electronics, vol. 20 (1990), pp. 1517-1522).

Chen, Y. et al., "Ratio-Based Decisions and the Quantitative Analysis of cDNA Microarray Images" Journal of Biomedical Optics, SPIE, Bellingham, WA, US, vol. 2, No. 4, Oct. 1997, pp. 364-374, XP002303971 ISSN: 1083-3668.

Jaekel et al., "Quantum Limits in Interometric Measurements" (Europhysics Letters, vol. 13 (1990) p. 301-306).

European Patent Office, EP Application No. 05857931.9-2201, Aug. 4, 2010, 4 pages.

Sommermeyer, Katrin, Authorized Officer, European Patent Office, International Search Report & Written Opinion, PCT Application No. PCT/US2005/031382, Nov. 17, 2006, 10 pages.

\* cited by examiner

DETECTING EVENTS OF INTEREST USING QUANTUM RESONANCE INTERFEROMETRY

CROSS REFERENCE TO RELATED APPLICATIONS

This application claims the benefit of the priority of U.S. Provisional Application Ser. No. 60/606,471, filed Sep. 2, 2004 and entitled "TECHNIQUE FOR ACTIVE SIGNAL PROCESSING BASED ON DYNAMICAL MODELS FOR ARRAYED PLATFORMS".

BACKGROUND

The subject matter described herein relates to signal analysis and applications for enhancing data characterization.

Experimentally acquired data typically includes noise in addition to signals representing information and/or events of interest. The noise represents undesired variations that are not related to the desired data. For example, the acquired data can include stochastic variations generated by interactions with the environment surrounding a measured system or a detector acquiring the data. Noise can be generated within the measured system by events that are unrelated to the information of interest. Noise may also be generated when the acquired data is transmitted or processed, for example, when it is digitized. Noise can be a significant problem with devices employing an array of sensors in which there are numerous sources of signals.

For example, biological molecules can be analyzed by biochips or mass spectrometers. In mass spectroscopy, large molecules in a source sample are ionized, fragmented and transported for mass analysis using electromagnetic fields. The measured mass spectrum is distorted by noise that is generated by variations in the generated ions or fragments, or fluctuations and inhomogeneities of the electromagnetic fields.

Biochips are microarrays of biological detectors (probes) to detect biological materials, such as oligonucleotides, peptides, cDNAs, mRNAs or proteins. High-density microarrays include a large number of probes on a single substrate. For example, a microarray can include hundred to a million spot, where each spot represents a particular type of probe. A spot can include one to a thousand million probe molecules that are complementary to a particular biological material. In a microarray experiment, sample molecules are labeled with fluorescence or other photoactive dyes. The labeled molecules hybridize with the complementary biological detectors in the microarray, and a result of the hybridization is determined by scanning photoactivity in the microarray. The scanned photoactivity is distorted by noise that is generated by defects in the microarray, non-complementary hybridization or resolution of the scanning.

Techniques to detect, measure and process signal in noisy data include traditional "passive" techniques. Passive noise analysis estimates a noise level in the data, and identifies signals that are above the noise level. For periodic signals, noisy data is transformed into a frequency (Fourier) representation in which noise components are estimated at multiple frequencies. Signals are detected at frequencies where the frequency component of the noisy data is larger than the estimated noise component. For non-periodic signals that depend on a time or a space coordinate, the noise level is estimated from temporal or spatial fluctuations, respectively. If the shape of the signal is known, the noisy data can be filtered based on the known shape, and a signal can be detected if the filtered data has a component above the noise level. Passive techniques also include maximum a-posteriori (MAP) techniques, maximum likelihood estimator (MLE) techniques, singular value decomposition (SVD), parametric distributional clustering (PCA), neural networks, fuzzy logic systems and Bayesian inferencing systems.

Some physical systems (hardware-based systems) use "active" signal processing. Active signal processing actively enhances signals that are below the noise level. In these systems objects of interest are detected through their interaction with particular excitations. For example, intelligent radars irradiate a moving object, such as an aircraft, with radar pulses that interact with the object and the reflection is received by an antenna. The object is identified by comparing the received signals against a background that is defined by previously transmitted signals. Another example is a superconducting quantum interferometric device (SQUID), in which coupled superconductive half rings are excited to detect magnetic fields. Other examples include imagery intelligence (IMINT), signals intelligence (SIGINT) and electronic intelligence (ELINT) devices. Active signal processing has also been performed by techniques using femto-lasers. However, while hardware-based signal processing systems allow one to characterize signals that would otherwise be obscured by noise using passive techniques, such systems are costly to manufacture and operate and can require several minutes to make a single measurement. In addition, active signal processing techniques may only be used during an experiment and do not permit the characterization of previously obtained experimental data.

It can therefore be appreciated that a need remains for a technique to characterize signals of interest both above and below noise thresholds that can make rapid measurements of both retrospective and prospective data sets, and that does not require expensive hardware.

SUMMARY

The present disclosure describes techniques for forming a model of noise, in one embodiment, a quantum expressor function, allows the acquisition of signal values even when their level is below the level of the noise. One aspect of the described techniques allows signal analysis using a noise model that can be embodied solely in software.

Implementations can realize one or more of the following advantages.

In an embodiment, a signal can be identified in experimentally acquired data in which noise level exceeds the signal. The signal can be identified even if the noise level is larger than the signal level, and may be particularly useful when the noise is ten to thousand times stronger than the signal. Thus for data relating to biological materials, such biological materials can be efficiently detected and quantitated in a noisy environment, such as a biological microarray that is exposed to a biological sample. A biological material can be detected in the sample even if the material's signal is below the noise level in the acquired data.

Signals below the noise level can be detected for a large number of different microarray types, including glass based, thin film, electronic, bead or quantum dot arrays. The signal analysis is not limited to particular methods or apparatus that are used to acquire the data. The data can be acquired by scanning techniques using a laser scanner or a CCD array, and biological molecules can be marked with fluorescence, chemiluminescence, bioluminescence and photoluminescence dyes. Noise can be analyzed in reference samples to define a non-linear dynamical model for signal analysis. The non-linear dynamical model can be defined "offline," i.e., before analyzing actual samples. The same non-linear dynamical model can be used for the same pre-characterized platform. Thus the same model can be used for samples that have the same type of array and dye and the same technique is used to scan the array. With the present techniques, a large number of samples can be analyzed in a short time.

The subject matter described herein may be embodied in a method for analyzing data signals, the method comprising receiving one or more reference samples specifying data acquired in an pre-characterized platform, analyzing noise in the acquired data of the reference samples, designing a noise model based on the noise analysis, and specifying an expresser function that uses the noise model to computationally enhance signals in data acquired in the pre-characterized platform in samples other than the reference samples.

The subject matter described herein may also be embodied in a computer-implemented method for active signal analysis, the method comprising receiving a plurality of calibrated samples specifying data acquired in an pre-characterized platform, each calibrated sample being exposed to a controlled amount of an active agent, analyzing noise in the acquired data of the calibrated samples, identifying a plurality of features in the analyzed noise and, for each feature, a register corresponding to a range of the amount of the active agent, and defining a calibration function that specifies a separate functional component for each register, each functional component specifying an estimated amount of the active agent based on the feature corresponding to the register.

In other interrelated variations, the subject matter described herein is a system for characterizing digitized output data from a platform array detector, the system comprising, a preconditioner to transform the output data to a spectral representation and to transform the spectrally represented output data to be compatible with a predetermined dynamical system, a coupler to convolve the preconditioned output data with a predetermined expresser function, a resonance detector to detect one or more events of interest within the convolved output data, and a quantitator to associate a measurement magnitude with each detected event of interest.

In yet another interrelated variation, the subject matter described herein is a method for characterizing digitized output data from a platform array detector, the method comprising the steps of obtaining multiple reference output data samples having known quantitative measurements over a range of detected intensities, identifying a plurality of regions across the reference samples in which the quantitative measurement varies with detected intensities in a consistent fashion, modeling each of the regions to associate the quantitative measurement with detected magnitude, obtaining experimental output data samples having unknown quantitative measurements, and associating, for each of the experimental data samples, each of the detected intensities with a region and determining the quantitative measurement using the model for the associated region.

In one interrelated aspect, received incoming data may be used to initialize a dynamical system corresponding to a modality of the incoming data. This initialized dynamical system may be used to generate a measurement probe which may be injected into a quantum mechanical system. Thereafter, it may be determined whether the injection of the measurement probe into the quantum mechanical system results in a collapse of the quantum mechanical system. If that is the case, a presence of signal within the incoming data may be determined.

In some variations, the dynamical system may be initialized using a trajectory of the dynamical system that corresponds to the modality of the incoming data. With such a variation, the generation of the measurement probes may be based on a modification of the trajectory of the dynamical system. In addition, the measurement probe may be repeatedly injected into the quantum mechanical system for a number of iterations until the quantum mechanical system collapses. This number of iterations may be used to determine a signal magnitude.

In still a further interrelated aspect, a noise model may be coupled with an expressor function to generate a first intermediate data set. Additionally, incoming data may be coupled with the expressor function to generate a second intermediate data set. Thereafter, enhanced data may be generated based on a difference between resonances in the first intermediate data set and resonances in the second intermediate data set. From this enhanced data, one or more events of interest may be identified in the enhanced data.

In another interrelated aspect, a measurement probe may be injected into a quantum mechanical system. Thereafter, a presence of signal within incoming data may be based on a collapse of the quantum mechanical system. Optionally, a magnitude of the signal may be determined based on an amount of time between injection of the measurement probe and the collapse of the quantum mechanical system.

In yet another interrelated aspect, sample data may be received from an arrayed platform that characterizes one or more events of interest and which contains signals associated with at least one of the events of interest having an intensity less than a noise threshold. Subsequently, the sample data may be interferometrically enhanced until a resonance occurs for the signals. A magnitude for each of the events of interest may then be determined based on an amount of time before the corresponding signal resonates. In some examples, the interferometry is quantum resonance interferometry or stochastic resonance interferometry.

An interrelated system may comprise a two-state bistable system (e.g., a two state quantum mechanical system), a noise reservoir, an excitation unit, and a resonance detection unit. The noise reservoir may characterize noise and be coupled to the two-state bistable system. The excitation unit may be operable to excite the two-state bistable system with sample data characterizing one or more events of interest. If the sample data is substantially similar to the noise reservoir, exciting the two-state bistable system results in substantially no change to at least one pre-determined property of the bistable system. On the other hand, if the sample data contains a component that is not substantially similar to the noise reservoir, exciting the two-state bistable system results a qualitative change in at least one predetermined property of the bistable system resulting in one or more resonances. The resonance detection unit is operable to detect resonances indicating an event of interest within the sample data.

The excitation unit may be operable to repeatedly excite the two-state bistable system until the two-state bistable system changes its state. The excitation may optionally be operable to measure a transition frequency between the two states of the two-state bistable system. In addition, a quantitation unit may associate a magnitude with the events of interest based on an amount of time for one or more resonances to occur. In some variations, the resonance detection unit determines that there are no events of interest present within the sample data after a predetermined number of excitations by the excitation unit. Moreover, the noise reservoir may be based on a Hamiltonian generated by a plurality of quantum oscillators. With such an arrangement, a frequency spectrum of the noise reservoir may be based on characteristic frequencies of the plurality of quantum oscillators.

In a further interrelated aspect, a plurality of calibrated samples specifying data acquired in an pre-characterized platform may received. Each of these calibrated samples may be exposed to a controlled amount of an active agent. Thereafter, noise in the acquired data of the calibrated samples may be analyzed. A plurality of features in the analyzed noise may be analyzed, and, for each feature, a register corresponding to a range of the amount of the active agent may be determined. Thereafter, a calibration function may be defined that specifies a separate functional component for each register, each functional component specifying an estimated amount of the active agent based on the feature corresponding to the register.

In another interrelated aspect, multiple reference output data samples having known quantitative measurements over a range of detected intensities may be obtained. In these reference samples, a plurality of regions may be identified in which the quantitative measurement varies with detected intensities in a consistent fashion. Thereafter, each of the plurality of regions may be modeled to associate the quantitative measurement with detected magnitude. After this modeling has been finalized, experimental output data samples may be obtained that have unknown quantitative measurements so that detected intensities for each of the experimental data samples may be associated with a region and the quantitative measurement using the model for the associated region.

Computer program products, tangibly embodied in information carriers are also described. Such computer program products may cause a data processing apparatus to conduct one or more operations described herein.

Similarly, systems are also described that may include a processor and a memory coupled to the processor. The memory may encode one or more programs that cause the processor to perform one or more of the method acts described herein.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

Like reference numbers and designations in the various drawings indicate like elements.

DETAILED DESCRIPTION

Figure 1:
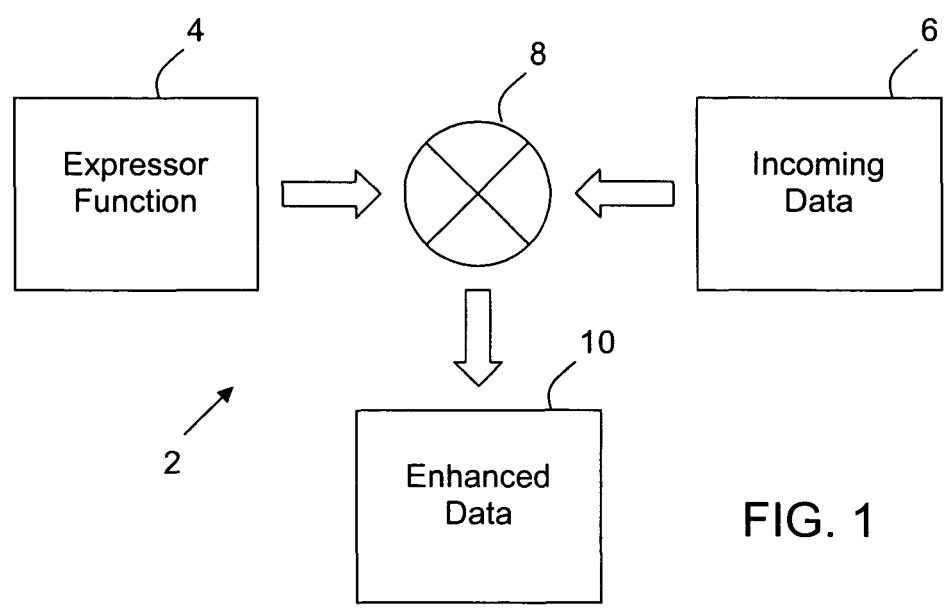
FIG. 1 is a schematic flow diagram illustrating a process of coupling of an expressor function with incoming data to result in enhanced data.

FIG. 1 illustrates a schematic flow diagram 2 in which an expresser function 4 (e.g., a quantum expressor function, etc.) is coupled 8 (e.g., interferometrically coupling of two stochastic systems, etc.) with incoming data 6 to result in enhanced data 10. Sample incoming data 6 may comprise single or multiple modality data (e.g., spatial, temporal, spatio-temporal, symbolic, spectral, spatio-spectral, audio, video, RF, etc.) characterizing one or more detector or data characterization elements, modifications to attributes, and/or events of interest. The enhanced data 10 may be used to identify one or more events of interest within the incoming data 6 that might not otherwise be identified without the coupling 8.

The enhanced data 10 may not have a linear relationship with the incoming data 6. The enhanced data 10 typically cannot be produced by application of a linear or series of linear transformations, higher order statistical (HOS) operator, generator function, or by using direct state-variable correlation operator, but rather, it is related to some invariant property of the physical platform and system used to produce the information (e.g., type of microarray, sample preparation protocol, scanner optics, and the like)

Within the framework of quantum resonance interferometry (QRI), a signal is considered to be an interference to noise. A signal denotes any event of interest while noise represents all events that are not a "signal", QRI entails construction of a noise model of the system wherein the expresser function 4 represents a "noise model" for the system for a prespecified target performance condition (e.g., detectability down to a given Limit of Detection (LOD)). The fidelity of the noise model or expressor function 4 is modality specific (e.g., collection of pixels on a focal plane, spectral segment of absolute abundance data for a mass spec detector, etc.) and corresponds to minimum amount of incoming data required to conclude signal presence. The incoming data 6 is initially assumed to be all noise. Interferometric computations between expression function and incoming data to generate resonances are used to detect signal as a departure to noise behavior.

---

The following mathematical steps are performed by the interferometric coupler using the preconditioned signal pattern:
$\overline{T}^{(0)}$ is defined as a vector containing the preconditioned components from an event of interest, and $\overline{T}^{(i)} = \overline{T}^{(i-1)} \overline{Q}^{(i)}$ where $Q^{(1)}$ represents is the QEF after i convolutions.
Thus $\overline{T}^{(1)} = \overline{T}^{(0)} \overline{Q}^{(1)}$
$\overline{T}^{(2)} = \overline{T}^{(1)} \overline{Q}^{(2)} = \overline{T}^{(0)} \overline{Q}^{(2)} \overline{Q}^{(1)}$
where $\overline{Q}^{(0)}$ represents the QEF developed in the preceding step and (its dimensionless quantity) and where $\overline{Q}^{(i)}$ represents the i-th perturbation to the QEF, induced by perturbing one of its spectral components.
for k = 1 to n
    for j= 1 to 1000 (set to a large counter value)
        perturb the $k^{th}$ component of QEF as below
        $Q^j(k) = [Q^{j-1}(k) + jC_1 \sin(w_0 j + C_1)]^+$ where $$[x]^+ = \begin{cases} x & \text{if } x \geq 0 \\ 0 & \text{if } x < 0 \end{cases}$$

and $$C_1 = \frac{1}{3}\left(\frac{2\alpha}{360}\right); \quad \alpha \text{ denotes a small constant;}$$

Let $w_0$ = the variance computed from the values $$\frac{\bar{f}_{pc}}{\text{Max}(\bar{f}_{pc})} \text{ where } f_{pc} \text{ denotes the preconditioned spectral}$$

vector corresponding to a known event of interest present in the arrayed pattern being analyzed.

As an example, $f_{pc}$ refers to the spectral components of the positive control.

The convolution iteration can be expressed as:

$$R_{kj} = \frac{\bar{f}^{(j-1)} \cdot \bar{Q}^j}{f_{nc}^{(j-1)} \cdot \bar{Q}^j}$$

where $f_{nc}$ refers to the spectral components of a canonical negative control, or preconditioned footprint of an event of interest known to be absent in the arrayed image.

After each convolution iteration check for monotonicity of $$\frac{R_{kj+2}}{R_{kj+1}} > 1 \quad \text{AND} \quad \frac{R_{kj+1}}{R_{kj}} > 1$$

if yes → then exit loop to perform global QEF iterations
    (that means this particular k component is important, i.e we are diverging from the negative control.)
    If no → then continue
end j loop
end k loop Global QEF iterations may be performed if monotonic divergence is detected between the preconditioned extraction core being analyzed and the canonical negative control, then the same convolution coupling operations are repeated for all the spectral harmonics. The global QEF iterations are provided by
Set $\bar{r}^0 = \bar{q}^{(j+2)}$
For m = 1 to 25 (chosen to be a small count value)
Compute
$$\bar{r}^m = \bar{r}^{m-1} + (m+j)C_1 \sin(\omega_0(m+j) + C_1) + mC_2 \sin(\omega_{1m} + C_2)$$

where $\omega_1$ captures the variance of the components of $$\frac{\bar{f}_{Nc}}{\text{Max}(\bar{f}_{Nc})}$$

and $$C_2 = C_1 + \varepsilon\left(\frac{\text{Parseval Avg from Pos. Con. PM}}{\text{Parseval Avg from Neg. Con PM}}\right)$$

where Parseval Avg. from Pos. Con. PM refers to the parseval number for a canonical event of interest known to be present, and Parseval Avg. from Neg. Con. PM refers to the parseval number for a canonical event of interest known to be absent.

and $\varepsilon$ is chosen to be small, 0.0001.
Again after each coupler iteration compute the term $$R_m = \frac{(\bar{f}^{j+m-1}) \cdot (\bar{r}^m)}{(\bar{f}_{Nc}^{j+m-1}) \cdot (\bar{r}^m)}.$$

Successively compute $R_m, R_{m+1}, R_{m+2} \ldots$

After each convolution iteration check if $$\frac{R_{m+2}}{R_{m+1}} > 1 \quad \text{AND} \quad \frac{R_{m+1}}{R_m} > 1$$

If the conditions of the above test are met, resonance is concluded and event of interest is called present.
If the monotonicity test fails, them the preconditioned test pattern is normalized using the expressions below.

$$\text{if } \bar{f}^{(j)} - \bar{f}^{(j-i)} > \bar{f}_{pc}^{(g)} - \bar{f}_{Nc}^{(c)} \text{ for any component}$$

$$\text{then } \bar{f}^{(j)} = \bar{f}^{(j)} - \left(\frac{\sum \bar{f}^{(j)} - \sum \bar{f}^{(j-1)}}{25}\right)$$

The above assumes an object with 25 spectral harmonics of interest.
The detailed equations for the coupler unit and resonance detector unit are given below:
for j = 1 to N $$\Delta j \to j+1 = \frac{\sum (f_i \cdot \hat{Q}^{j+1,pm})}{\sum (NCF_i^{0,pm} \cdot Q^{j+1})} \Big/ \frac{\sum (f_i^{o,pm} \cdot Q^{j,pm})}{\sum (NCF_i^{g,pm} \cdot Q^{j,pm})}$$

$$QEF_{r+1} = \left\{QEF_r + A(j,r) + \frac{B}{r}\right\}$$

where $B = f(w_1)$ and $$W_1 = \sigma\left(\frac{\sqrt{PSD_{pm,njc}}}{\sqrt{\text{man } PSD_{pm,njc}}}\right)$$

$A = \phi_c(j+r) \cdot \{\sin(w_o(j+r) + \phi_c)\}$ $B = \phi_{c_1} r) \cdot \{\sin(w,(r) + \phi_{c^1})\}$ $\phi_{c^1} = \phi_c + \varepsilon\left(\frac{\sigma_1}{\sigma_2}\right)\{=0.0001\}$ $Q^{j+1} = \hat{Q}^j$
$j \neq k$ $$Q^{j+1}_{i=k} = \left[\hat{Q}^j_{i=k} + (\phi_c \cdot j)\sin(w_0 j + \phi_c)\right]$$

Check $\dfrac{\Delta^2_{j-1,j+2}}{\Delta j} > 1$ $$\frac{\Delta j+1 \to j+2}{\Delta j \to j+1} > 1 \Big| \frac{\Delta j \to j+1}{\Delta j \to j-1} > 1$$

$\phi_c = \dfrac{1}{3} \cdot \dfrac{2\pi}{360}$ $$W_0 = \sigma\left(\frac{PSD_{QEFpc,pm}}{\max(PSD_{QEF;pc,pm})}\right)$$

$$W_1 = \sigma\left(\frac{PSD_{QEF,NC,pm}}{\max(PSD_{QEF,NC,pm})}\right) w_0 \approx w_1$$

Resonant Marker Identification

Finally, resonance marker detector performs the following mathematical calculations using the convolved signal pattern to identify the events of interest within the convolved signal pattern.

The resonant iteration is terminated when $$\frac{\Delta^2_{j-1,j+2}}{\Delta j} > 1$$

-continued $$\frac{\Delta j+1 \to j+2}{\Delta j \to j+1} > 1 \left| \frac{\Delta j \to j+1}{\Delta j \to j_{-1}} > 1 \right.$$

or when iteration counter t exceeds preset "N" (e.g., $10^3$ iterations) (for digital approximation to analog dynamics).

Figure 2:
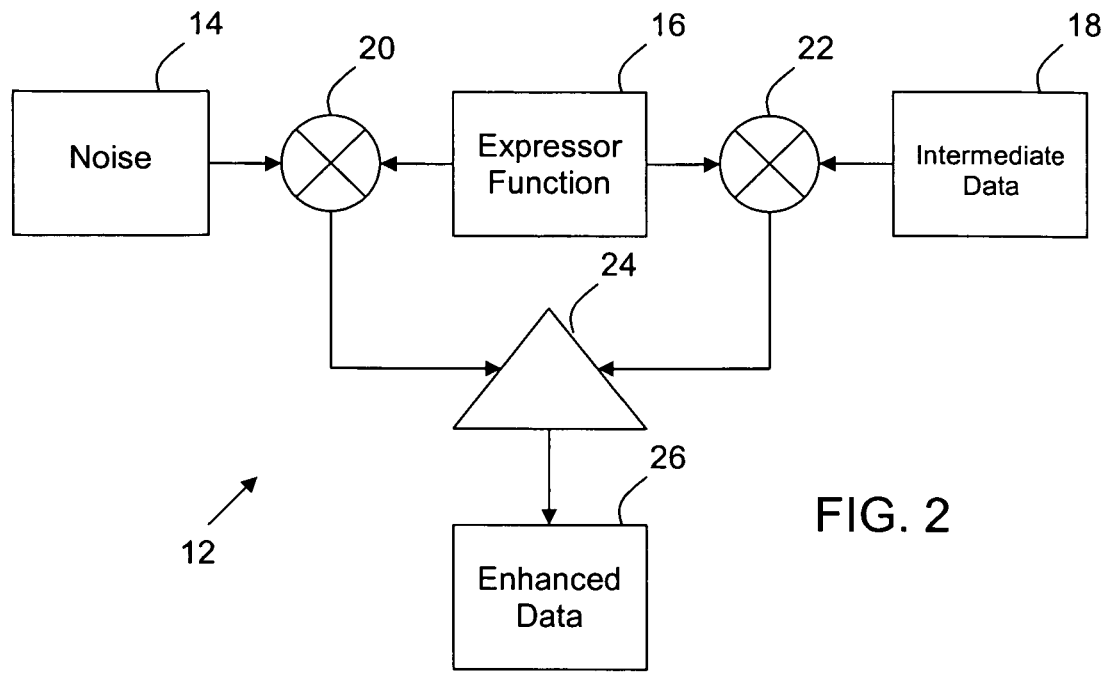
FIG. 2 is a schematic flow diagram illustrating a process in which a differential measurement is utilized to generate enhanced data.

FIG. 2 illustrates a schematic flow diagram 12 in which a noise model 14 may be coupled 20 with an expressor function 16 to generate a first intermediate data set. In addition, the expressor function may be coupled 22 with incoming data 18 to generate a second intermediate data set. A difference between the first intermediate data set and the second intermediate data set may be generated at 24 to result in enhanced data 26. Such differential measurements may provide robust measurements which reduce the number of false negatives and positives within the enhanced data 26 so that events of interest may be identified and quantified.

Figure 3:
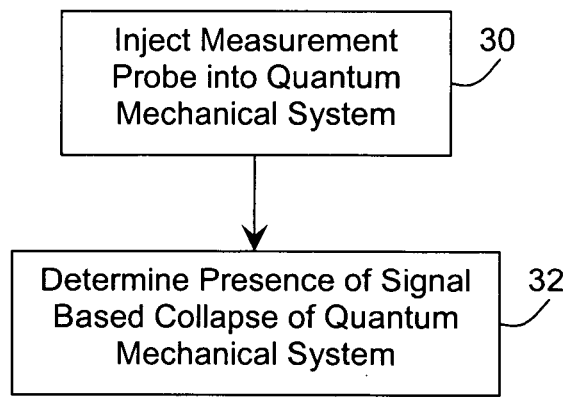
FIG. 3 is a schematic flow diagram illustrating a process by which an injection of a measurement probe causes a quantum mechanical system to collapse.

FIG. 3 illustrates a process flow diagram 28 in which a measurement probe may be injected, at 30, into a quantum mechanical system. Thereafter, a presence of signal within the detection data may be determined, at 32, based on a collapse of the quantum mechanical system. In some variations, a magnitude of the signal may be determined based on an amount of time between the injection of the measurement probe and the collapse of the quantum mechanical system.

Figure 4:
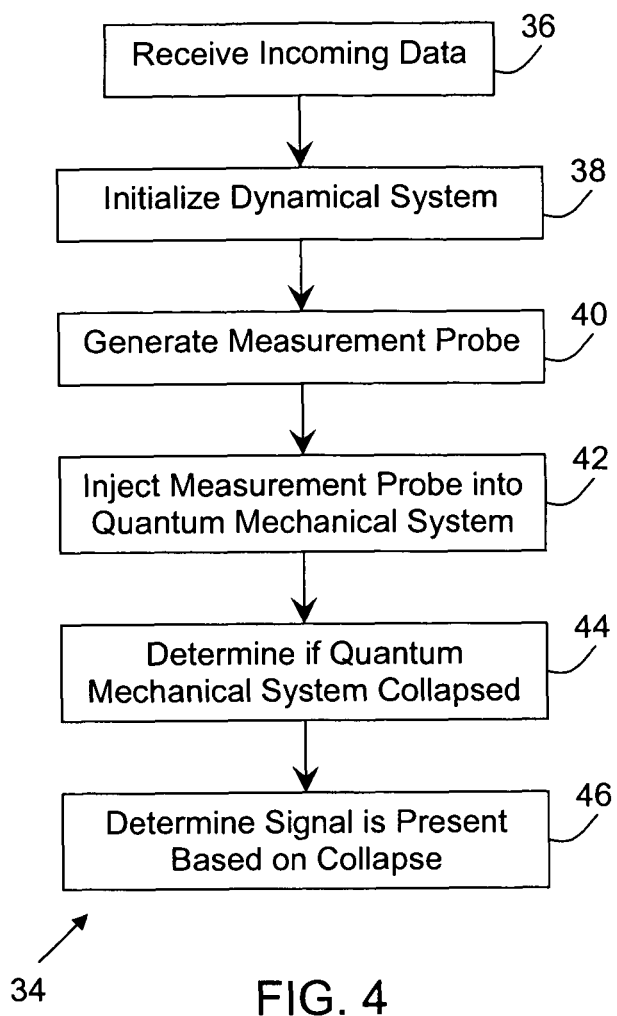
FIG. 4 is a schematic flow diagram illustrating a process for determining if signal is present within incoming data.

FIG. 4 illustrates a process flow diagram 34 in which, at 36, incoming data may be received. Using this incoming data, at 38, a dynamical system may be initialized corresponding to a modality of the incoming data using the incoming data. Subsequently, at 40, a measurement probe may be generated based on the initialized dynamical system. This measurement probe may be injected, at 42, into a quantum mechanical system. It may then be determined, at 44, whether the injection of the measurement probe into the quantum mechanical system results in a collapse of the quantum mechanical system. If it is determined that the quantum mechanical system has collapsed, at 46, it is then determined that a signal is present within the incoming data. In some variations, the initializing at 38 may comprise initializing a trajectory of the dynamical system corresponding to the modality of the incoming data using the incoming data and the generating, at 40, may comprise generating the measurement probe based on a modification of the trajectory of the dynamical system.

Figure 5:
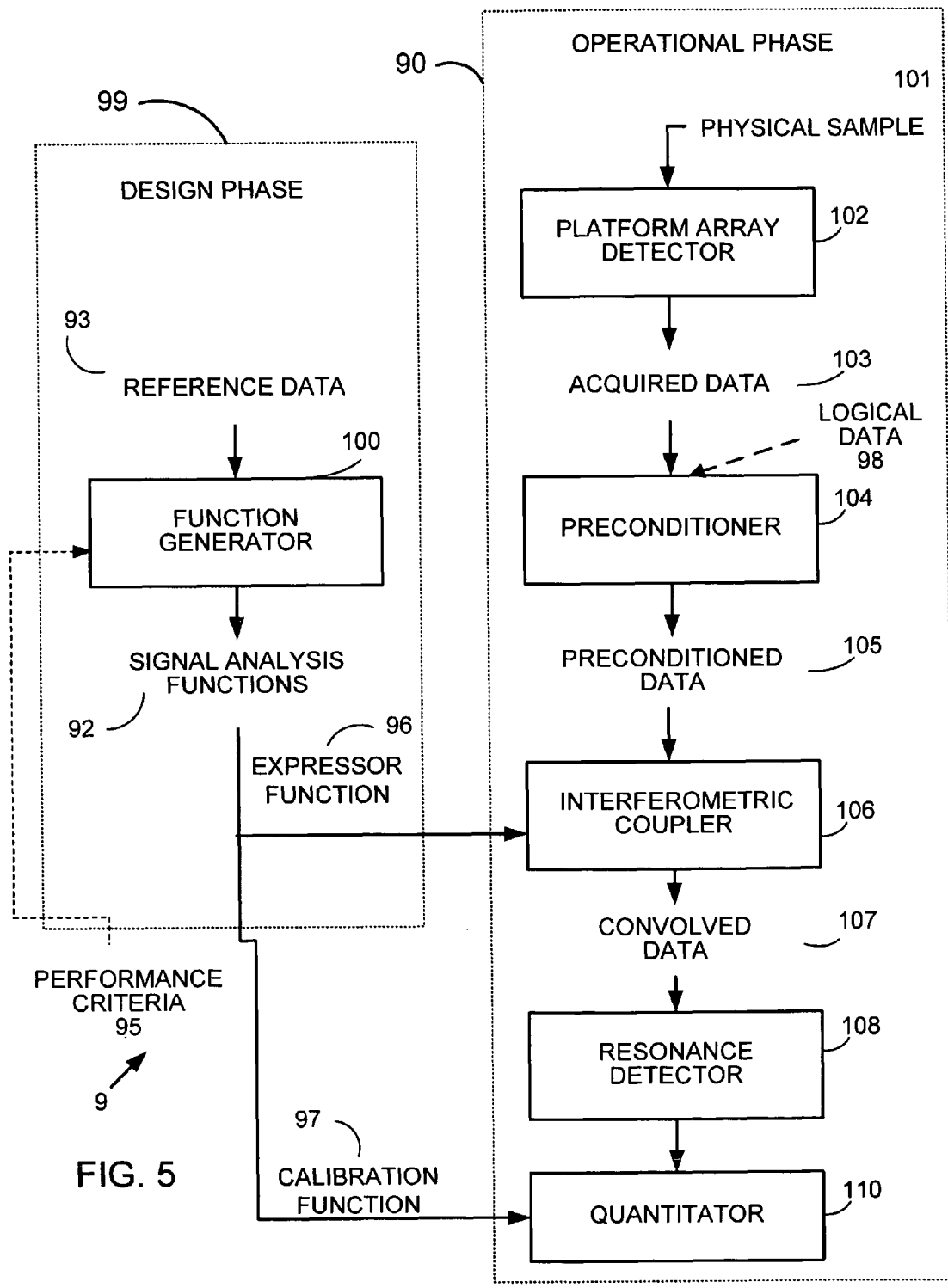
FIGS. 5, 5A and 6 are schematic block diagrams illustrating systems for analyzing signals that are below noise level.

FIG. 5 illustrates a block diagram of a system 9 used herein to carry out the signal analysis. In one variation, the system 9 is an open-loop interferometric system. The operation of the system 9 is divided into a design phase 99 and an operational phase 90. In the design phase 99, signal analysis functions 92 are determined for a particular experimental platform that is used in the operational phase 90. The signal analysis functions 92 are used in the operational phase 90 by an interferometric computational system to analyze events of interest (e.g., physical samples, data stream mining, etc.) associated with the particular platform. During the operational phase 90, a large number of data sets can be analyzed that are derived from the particular platform using the same signal analysis functions 92. For each other platform as well as modifications to platforms, new signal analysis functions can be generated or existing signal analysis functions 92 may be adapted.

In the design phase 99, a function generator 100 receives reference data. The reference data includes platform data that characterizes a platform in which the physical samples are analyzed. The platform data may include platform calibration data and platform array characteristics (associated with events of interest). For example, the platform can be specified by a particular detection method for a genomic biochip or microarray that includes a particular array of known gene expressions. As another example an imaging platform for high throughput cellular screening may be specified by a particular CCD imager and fluorescence dye system. The corresponding platform data specifies the layout of the array and noise that is generated when various features are detected in the array. The reference data can also include calibration data that are generated by known events of interest in the particular platform. For example, the calibration data can include data that is acquired in the platform from a set of specially prepared physical samples.

In some variations, the function generator 100 may also receive or otherwise be associated with performance criteria 95 which establishes desired target specifications such as limit of detection, limit of quantitation, precision, resolution, specificity, accuracy, signal to noise, and the like.

Based on the reference data, the function generator 100 generates signal analysis functions 92. In one variation, the generated functions 92 include expresser functions 96 for interferometric signal analysis, such as quantum expressor functions and stochastic resonance functions. For reference on signal analysis using quantum expressor functions and stochastic resonance functions and their generation, see U.S. Pat. Nos. 6,142,681 and 6,136,541 both to Dr. Sandeep Gulati, and both of which are hereby fully incorporated by reference. The expresser functions 96 are based on a dynamical model, and can be used to actively enhance signal in data acquired from the physical samples. The expressor functions 96 are based on how a dynamical system responds to excitations that are correlated with a signal to be enhanced or with a noise that is typical in the platform. The signal analysis functions 92 also include calibration functions 97 for quantitating signals that are detected in the acquired data.

The operational phase 90 involves a platform array detector 102 receiving a physical sample 101 to produce acquired data 103. The operational phase 90 also involves a preconditioner 104, an interferometric coupler 106, a resonance detector 108 and a quantitator 110. The platform array detector 102 acquires data from the physical sample 101, such as a biochip or another microarray. The platform array detector 102 is a physical detection device, such a laser scanner or a CCD array. In alternative implementations, the physical sample 101 can represent any other object of interest and the platform detector 102 can include a corresponding detector. For example, charged biomolecules can be detected with a mass spectrometer.

The acquired data 103 is sent to the preconditioner 104, which preprocesses the acquired data 103. Optionally, logical data 98 may be provided directly to the preconditioner 104 thereby obviating the requirement for the platform array detector 102. For example, the preconditioner 104 can filter the acquired data 103, and convert the filtered data into a spectral domain. Techniques for converting the signal pattern to a spectral domain are described in U.S. patent application Ser. No. 10/430,664 entitled "Method and System for Characterizing Microarray Output Data" to Dr. Sandeep Gulati, filed on May 5, 2003, which is hereby fully incorporated by reference in its entirety. The preconditioner 104 generates preconditioned data 105 in which spectral harmonics are selected as required by the expresser function 96 generated by the function generator 100. For example, spectral harmonics can be selected according to events of interest in a predetermined dynamical system.

The interferometric coupler 106 applies one or more expressor functions 96 to the preconditioned data 105, and generates convolved data 107. In the convolved data 107, signals are enhanced relative to the noise level due to nonlinear interferometric effects defined by the expressor functions 96, as discussed in more detail with reference to FIGS. 10-12.

The resonance detector 108 processes the convolved data 107 to identify particular events of interest, if any, appearing within the convolved data 107. Based on the identified events, the resonance detector 108 can detect if a signal is present in the acquired data 103. Due to the signal enhancement in the interferometric coupler 106, signals can be detected in the convolved data even if noise is several magnitudes (e.g., ten to ten thousand times and more) larger than the signal in the acquired data 103.

Optionally, the quantitator 110 operates to quantitate the detected signal. The quantitator 110 uses a calibration function 97 received from the function generator 100 to calculate a corresponding quantity from the detected signal. For example, the detected signal can indicate that a particular gene is present in a biological sample, and the quantitator 110 can estimate the amount (or density) of the particular gene based on a respective calibration function 97.

Thus components of the operational phase 90 precondition and transform the acquired data 103 into a spectral object. In parallel (or previously), components of the design phase 99 generate the expressor functions 96 which are based on a spectral function that is optimized for a particular kind of arrayed platform and characterizes and captures the noise invariance of that arrayed platform. The spectral object of the acquired data 103 and the expressor functions 103 are caused to interfere by the interferometric coupler 106 to determine whether the interference converges to a resonance or not. If interference occurs (e.g., resonance), then it may be determined that an event of interest is present within the acquired data 103. Moreover, the behavior of the convergence may be characterized and used for quantitation measurements.

Figure 5A:
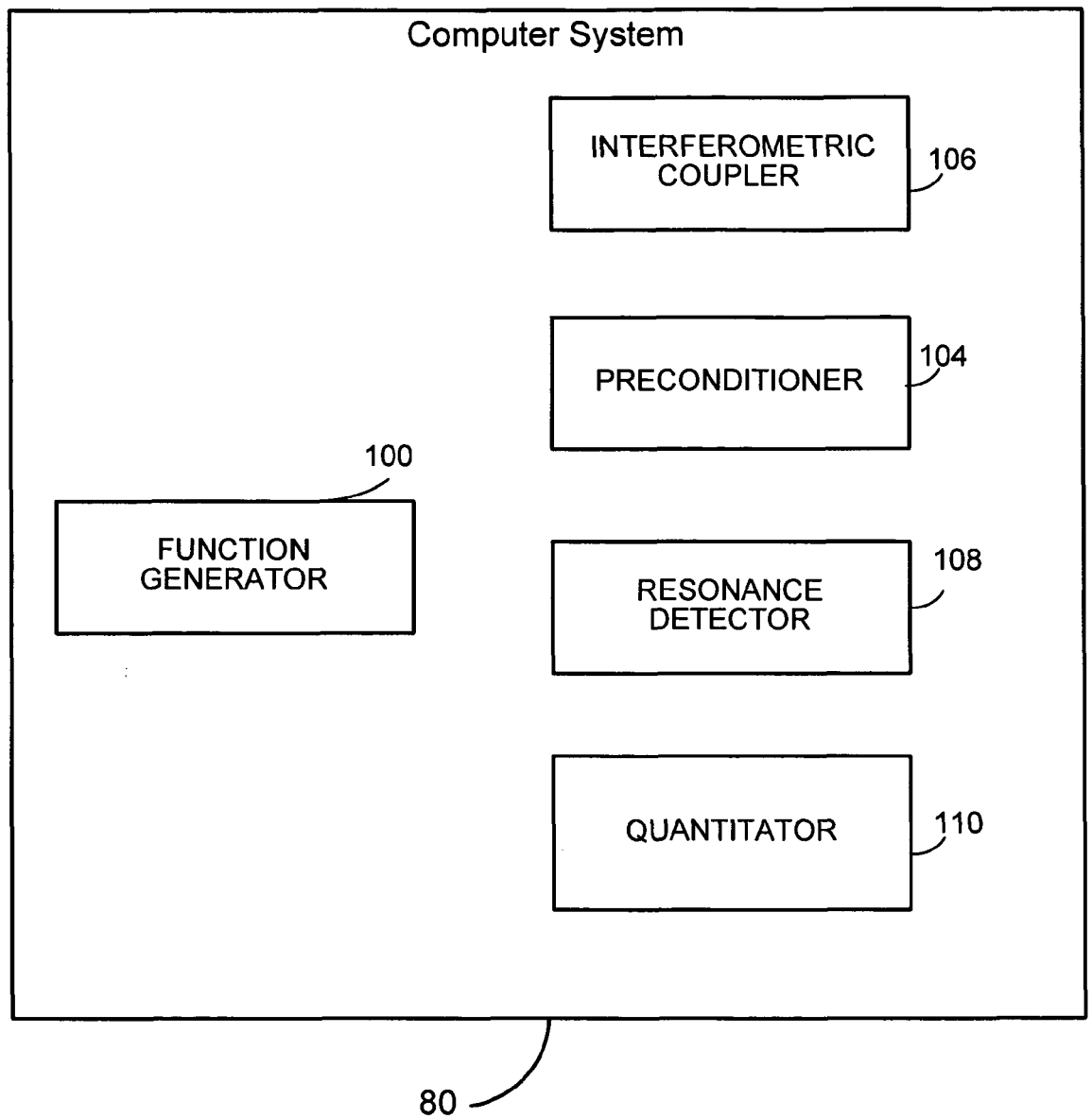

As shown in FIG. 5A, with the exception of the platform array detector 102, which is a physical measuring device, all other components illustrated in FIG. 5 may be implemented in a computer system 80 in software, hardware, firmware, programmable device physics (such as thermal control of smart material properties), or biophyiscs (example controlling chemical composition to facilitate biological events), or some combination thereof. The computer system 80 can include one or more computers or other data processing apparatus. In particular, each component may be a computer product including instructions to perform the corresponding operations. In one example, each component is a software module operating within a single generally programmable computer. In other cases, the software modules are implemented using separate microprocessors or application specific integrated chips (ASICs). In still other examples, some of the components are implemented in software whereas others are completely hard-wired.

Figure 6:
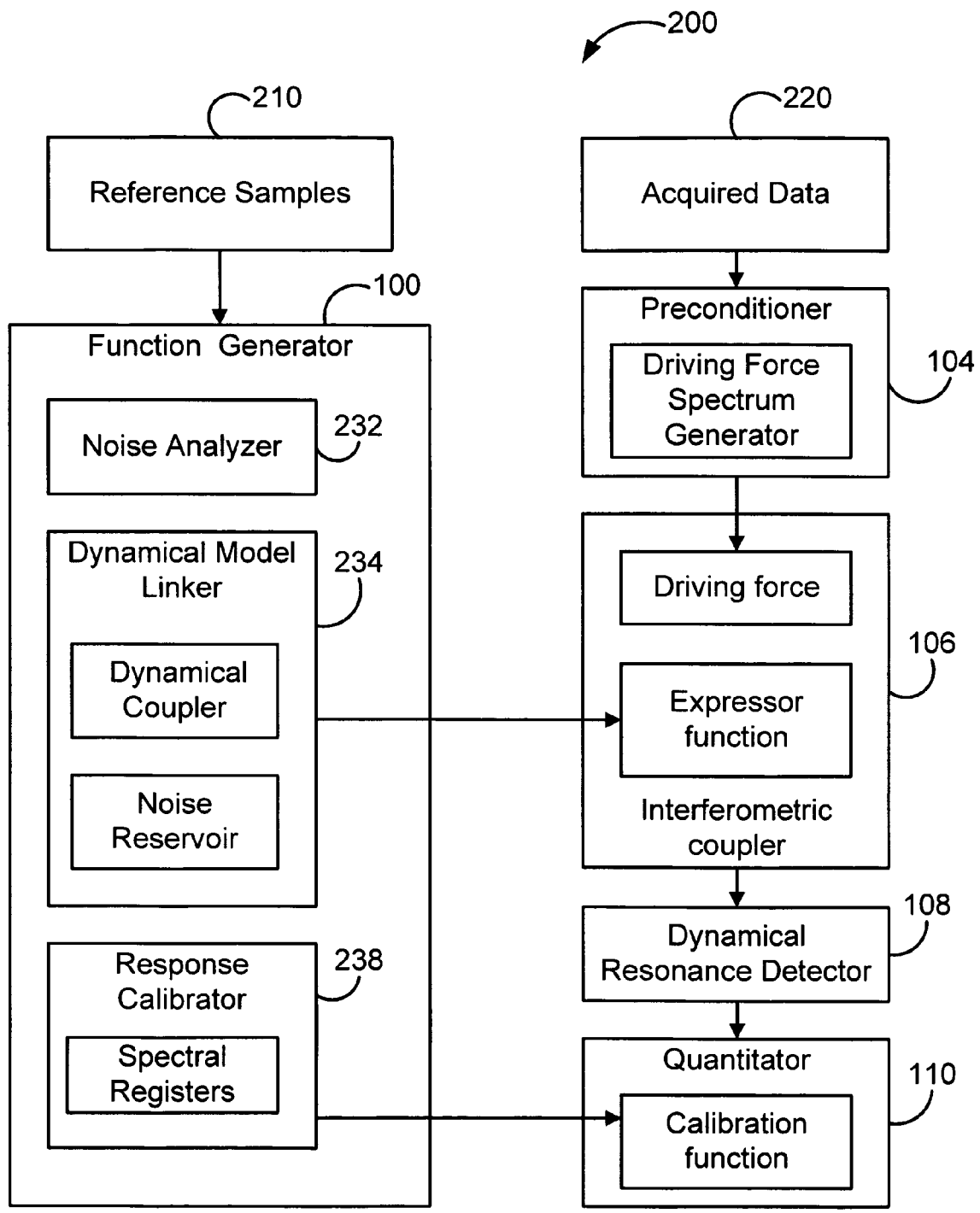

FIG. 6 illustrates an implementation of elements that can be used in the design phase 99 and operational phase 90 shown in FIG. 5. Accordingly, reference samples 210 are processed by the function generator 100 in the design phase, and acquired data 220 is processed by the preconditioner 104, the interferometric coupler 106, the dynamical resonance detector 108 and the quantitator 110 in the operational phase.

The reference samples 210 and the acquired data 220 correspond to experimental data acquired on the same pre-characterized platform. The pre-characterized platform is defined by the type of physical samples and detection techniques that are used to measure the samples. The pre-characterized platform can include biomolecular, biomechanical, optical, ionic, optoelectronic, radio frequency or electronic microdevice platforms.

For example in a biological array, various probes are attached to a solid substrate, such as glass, nylon, thin film and polymer. The substrate has a certain layout represented by feature size, various controls (positive, negative dye and alignment), and probe density. The probes can include one or more of cDNA, mRNA or oligonucleotide proteins, peptide or oligopeptide probes. Exemplary biomolecular spatial arrays include: hybridized spotted cDNA microarrays, synthesized oligonucleotide arrays, spotted oligonucleotide arrays, peptide nucleotide assays, single nucleotide polymorphism (SNP) arrays, carbohydrate arrays, glycoprotein arrays, protein arrays, proteomic arrays, tissue arrays, antibody arrays, antigen arrays, bioassays, sequencing microarrays, sequencing by hybridization (SBH) microarrays, siRNA duplexes, RNAi arrays glass-based arrays, nylon membrane arrays, thin film arrays, polymer-substrate arrays, capillary electrophoresis arrays, genospectral arrays, electronic arrays, bead arrays, quantum dot arrays, glycan arrays, spotted wells, and spotted well plates. These arrays may be implemented as a microarray.

Figure 8:
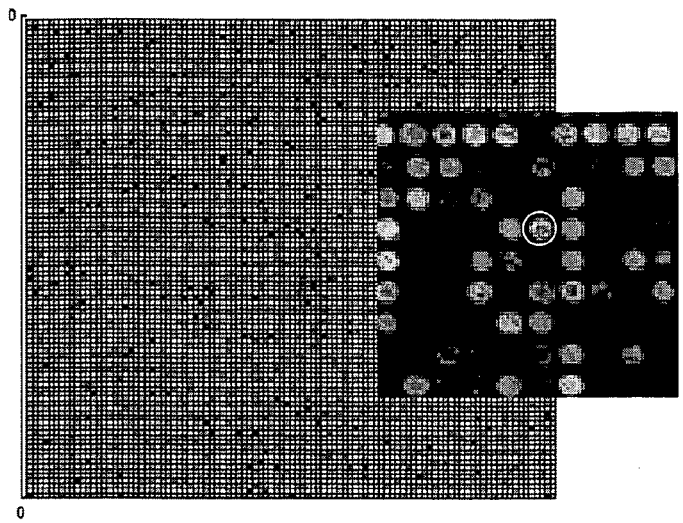
FIG. 8 is a schematic diagram illustrating acquired data in a biochip.
Figure 8:
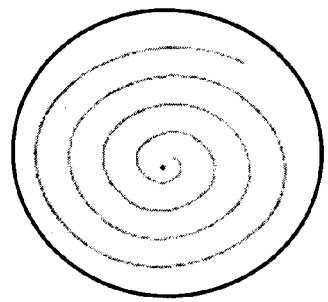

After the biological array is exposed to a biological sample, such as blood or urine, the probes hybridize with one or more biological material in the sample. The sample is labeled by one or more dyes to detect hybridization by a detector of the platform. A wide variety of detectors (and corresponding platforms) may be used to acquire data from the biological array. For example, the platform detector can include laser scanners, confocal microscopy detectors, charge coupled devices (CCDs) and electronic readouts. Exemplary data acquired from a biological array is shown in FIG. 8.

The reference samples 210 can include no-signal samples, false-signal samples and true-signal samples. A no-signal sample has no active agent. For example, a biochip designed to detect genes can be exposed to a biological sample that includes no genes at all, and the exposed biochip can be processed according to the pre-characterized platform to generate a no-signal sample. A false signal-sample includes one or more non-specific agents. For example, a biochip for human genes can be exposed to non-human genes, which may produce hybridization patterns due to partial match with human genes. A true-signal sample includes one or more active agents. The true-signal sample can be a calibrated sample that is exposed to a controlled amount of active agent.

In the design phase, the function generator 100 generates functions, such as expressor functions and calibration functions, for signal analysis based on the reference samples 210. The function generator 100 includes a noise analyzer 232, a dynamical model linker 234 and a response calibrator 238.

The noise analyzer 232 analyzes noise in the reference samples. Optionally, the noise analyzer 232 first preprocesses data in the reference samples. The preprocessing can include oversampling or applying one or more filters. The oversampling can be performed using interpolation techniques, such as zero-padding high-frequency components. The applied filters can be used to decrease high frequency stochastic noise or to sharpen features of interest. In one implementation, the quality of data is improved using a Renka and Cline filter, in R. J. Renka and A. K. Cline, "Scattered data fitting using a constrained Delaunay Triangulation," IMACS Transactions on Scientific Computing 91, AI, Expert Systems, and Symbolic Computation, vol. 3, North Holland, 1992.

In one implementation, the noise analyzer 232 analyzes fluctuations in the reference samples 210 using a spectral representation, such as a Fourier representation. The noise analyzer 232 can identify a region for each probe in a sample. A probe corresponds to a particular feature of interest, such as a gene sequence, and includes multiple acquired data points, such as pixels in a laser-scanned image. For each probe, the noise analyzer 232 serializes the acquired data points according to a predetermined scheme, and Fourier transforms the serialized data to generate a frequency spectrum of the probe. The serialization scheme specifies an order for serializing the acquired data.

The noise analyzer 232 identifies typical noise in the pre-characterized platform based on frequency spectrum in no-signal or false-signal reference samples. For example, the noise analyzer 232 can identify a "noise signature" in the reference samples. The noise signature is defined by features of the noise that have small fluctuations from probe to probe. For example, the noise signature can include a portion of the noise that is characteristic to the pre-characterized platform.

The noise signature can be identified by comparing frequency spectrums of probes in no-signal samples, and identifying portions of the frequency spectrum that have small fluctuations. A tolerance can be defined for identifying noise signature. The tolerance specifies allowed probe-to-probe fluctuations in the noise signature, and can be based on design parameters, such as an optimal number of frequency components in the noise signature, a limit or range for signal detection. False-signal reference samples can be used to identify noise signatures for probes where the false signal modifies the noise spectrum. Techniques to identify the noise signature are discussed with reference to FIGS. 7 and 9.

The noise analyzer 232 can also analyze noise in true-signal samples using the same techniques as for no-signal or false-signal samples. Typically, the noise spectrum is different for true-signal samples from that of no-signal or false-signal samples. The noise spectrum of the true-signal samples can also depend on the strength of the signal. Such dependencies can be analyzed using calibrated samples, and the result of the analysis can be used for quantitation, as discussed below. The analysis of calibrated samples can also be used to set design parameters such as a lower or upper signal limit for which the signal detection is planned.

The dynamical model linker 234 defines an expresser function based on the noise signature and the design parameters. The expresser function describes a response to an excitation of a non-linear dynamical system, such as a two-state system. The non-linear dynamical system is coupled to a noise reservoir by a dynamical coupler. The noise reservoir has a frequency spectrum that is based on the noise signature identified by the noise analyzer 232. The dynamical coupler is defined such that, if the non-linear dynamical system receives an excitation whose spectrum corresponds to the noise signature of the platform, the excitation's energy is quickly absorbed in the noise reservoir through the dynamical coupler. If the spectrum of the excitation is different from that of the noise signature of the platform, the noise reservoir may be slow to absorb the excitation's energy. The excitation may even qualitatively change the state of the non-linear dynamical system.

Due to the slow decay of the excitation's energy, when the excitation includes a signal whose spectrum is different from that of the noise signature of the platform, the signal can be enhanced. If the excitation also includes a noise component of the platform, the signal will be enhanced because the noise is quickly absorbed in the noise reservoir. The signal enhancement depends on parameters of the dynamical system. The dynamical model linker 234 can set these parameters to optimize the enhancement or to achieve a particular limit of signal detection.

The expressor function can be used to calculate the system's response to excitations, thus it can be used to actively enhance signals. For some systems, such as a spin-boson model described with reference to FIG. 10, the expresser function can be explicitly calculated. For other dynamical models, the expresser function can be specified by an algorithm or an interpolation formula based on model simulations. Defining expresser functions is further discussed with reference to FIG. 7.

The response calibrator 238 defines a calibration function for signal quantitation. The calibration function describes the relation between a quantity, such as a concentration of an active agent in a sample, and a signal strength that is measured with active signal processing. For example, the signal strength can be measured by a resonance amplitude that describes how fast the signal in the sample is enhanced as the expressor function is applied. The calibration function is based on calibrated samples that are true-signal samples exposed to controlled amounts of the active agent.

The calibration function uses spectral registers. Each spectral register represents concentration range of the active agent, and specifies a spectral feature and corresponding region in the frequency spectrum of a sample. (The spectral register is not limited to the frequencies of the noise signature of the platform.) The frequency regions of the spectral register are selected by comparing the frequency spectrum of the calibrated samples, and selecting the portion of the spectrum that develops the spectral feature if the concentration is in the range corresponding to the register. Techniques to define and use spectral registers for quantitation are discussed with reference to FIGS. 9-11

In the operational phase, the acquired data 220 are processed by the preconditioner 104. The preconditioner 104 performs the same preprocessing steps as the noise analyzer 232. The preconditioner 104 includes a driving force spectrum generator that generates a frequency spectrum for a force that drives the dynamical system defined by the dynamical model linker 234. The preprocessed data is Fourier transformed to define a Fourier spectrum, and the force spectrum is defined by selecting those components of the Fourier spectrum that correspond to the frequencies in the noise signature of the pre-characterized platform.

The interferometric coupler 106 applies the expressor function defined by the function generator 100 to calculate responses of the corresponding non-linear dynamical system to excitations defined by the driving force spectrum. An exemplary dynamical system and its responses to excitations are discussed with reference to FIGS. 6 and 7.

The dynamical resonance detector 108 detects signals in the acquired data 220 based on a qualitative change in a dynamical quantity. The dynamical quantity is calculated based on the data generated by the interferometric coupler 106. Detecting signals using the expressor function is discussed in detail with reference to FIG. 12.

If a signal is detected by the resonance detector 108, the quantitator 110 uses spectral registers and a calibration function specified by the response calibrator 238 to quantitate detected signal. The quantitator 110 determines a resonance amplitude of a detected signal, selects a functional component according to the spectral registers, and uses the selected component of the calibration function to determine a quantitative value for the concentration of an active agent corresponding to the detected signal. Techniques for quantitating signals are further discussed with reference to FIG. 15.

Figure 7:
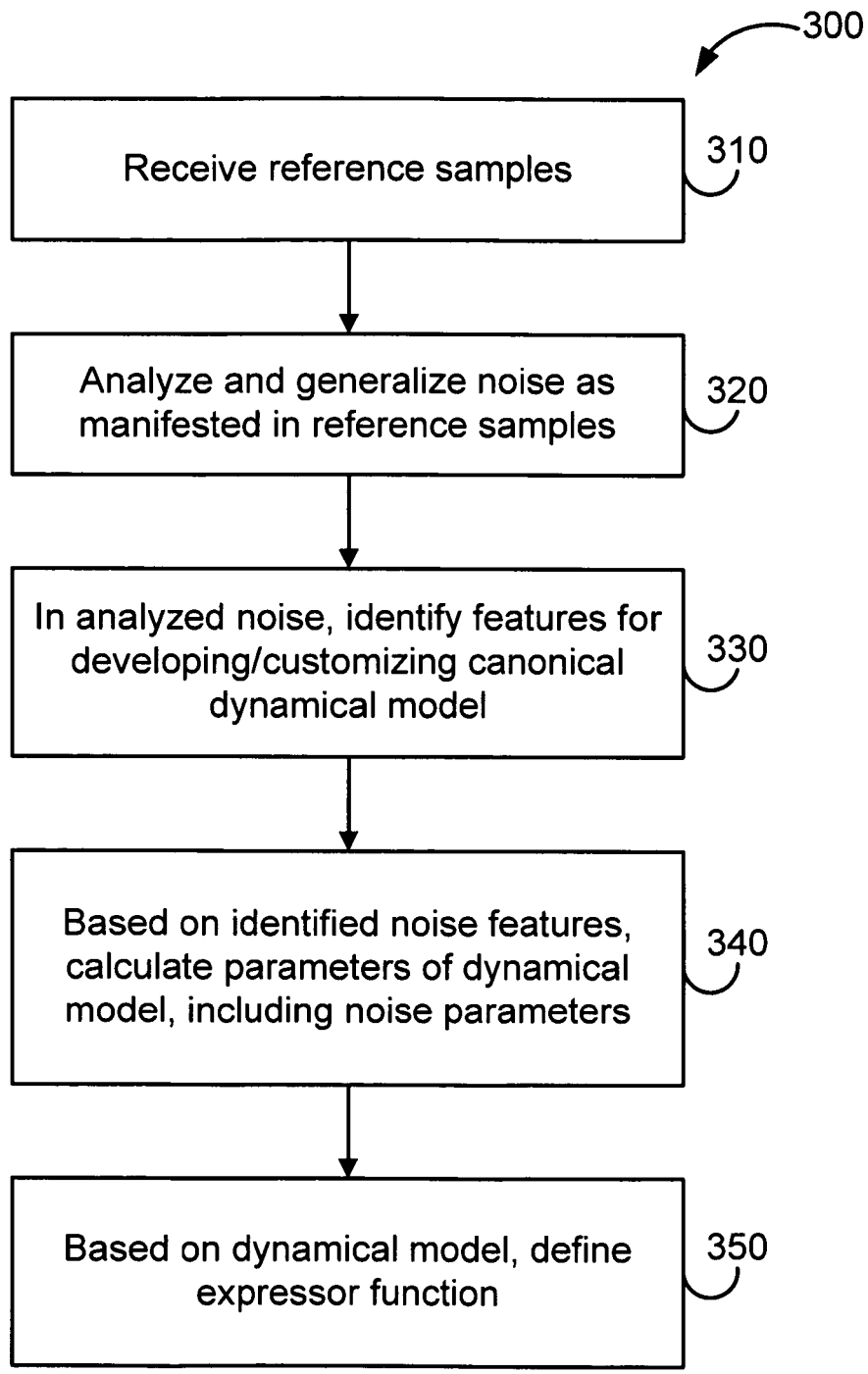
FIGS. 7, 13 and 15 are schematic flow diagrams illustrating methods for analyzing signals that are below noise level.

FIG. 7 illustrates a method 300 for generating expressor functions, such as quantum expressor functions for active signal analysis. The method 300 can be performed by a system including the function generator 100.

The function generator 100 receives one or more reference samples (step 310). The reference samples specify data acquired by a particular pre-characterized platform, such as data acquired from an arrayed platform such as a microarray for analyzing biological samples. The reference samples can include no-signal, false-signal and calibrated true-signal samples measured in the particular pre-characterized platform. Each sample can include a large number of probes, where each probe corresponds to a particular measurement, such as detecting a particular gene or sequence. Each probe can include multiple data points, such as pixels in a scanned image. An exemplary arrayed data output is illustrated in FIG. 8.

The function generator 100 analyzes and generalizes noise as manifested in the reference samples (step 320). In one implementation, the function generator 100 first identifies locations of different probes in the reference samples. For example, the function generator 100 can register a design map of a microarray with an actual sample, and use the registered map to identify different probes in the sample. Registration can be performed with standard techniques using grids or graph isomorphic algorithms. Alternatively or in addition to using a design map, the probe locations can be identified by extracting features such as spots, edges corners or boundaries in the sample.

Optionally, the acquired data in the reference samples can be preprocessed using one or more filters, such as Gabor filters, low and high pass filters, band filters, Laplacian filters or gradient filters. For example, these or other filters can be applied to an image specifying the acquired data by pixel values. The filters can enhance contrast or extract edges or other features in the image.

After identifying a probe, the system can define a data core for the probe. The data core is a portion of the acquired data corresponding to the probe in the sample. For a probe corresponding to a spot in a microarray, the data core can be defined by a circular region surrounding pixels that represent the spot in a scanned image of the microarray. The data core defines the data that will be used in any further analysis of the probe. The data core can be defined based on a design map or user input. Alternatively, the function generator 100 can determine the data core based on an analysis of the sample. The function generator 100 can also optimize the size of the data core based on the amount of information required for desired resolution and detection limits for the probe.

For each probe, the function generator 100 generates a sequence of data points from the acquired (or preprocessed) data in the core. The data sequence is generated according to a serialization scheme. For example, data can be ordered along concentric circles or an inward or outward spiral in a circular core. Or data can be ordered according to columns or rows in a rectangular core. In addition to ordering, the serialization scheme can specify a filtering or oversampling of the data on the core.

The function generator 100 transforms the generated data sequence into a spectral domain. For example, the function generator 100 can apply a fast Fourier transformation ("FFT") to the generated data sequence. The FFT provides a spectral representation that has the same number of frequency components as the number of points in the data sequence. In one implementation, the function generator 100 defines a spectral length, and uses interpolation and extrapolation techniques, such as zero padding, for data sequences that have a different length.

The function generator 100 defines a spectral representation of the data core based on the magnitude or phase of the FFT spectrum. In one implementation, the function generator 100 divides the data sequence of the core into n disjunctive or partially overlapping portions, and applies FFT to each portion. Optionally, the function generator 100 can convolute each Fourier transformed portion with one or more kernels to enhance spectral features. The function generator 100 calculates a spectral representation of the core using an average over the n Fourier transformed portions. For example, the function generator 100 can average the squared amplitude of each frequency component over the n portion to define the spectral representation. In alternative implementations, the function generator 100 can generate other spectral representations. For example, the spectral representation can be based on a two-dimensional Fourier transformation of the data in the core.

The function generator 100 identifies characteristic features in the analyzed noise (step 330). In particular, the function generator 100 identifies features that are typical to noise in the pre-characterized platform, but change if a signal is present. The identified noise features are used to develop or customize a canonical dynamical model that can be used for active signal processing.

In one implementation, the function generator 100 uses the spectral representation of probes in the reference samples to specify a noise signature of the pre-characterized platform. For example, the function generator 100 compares the generated spectral representation of multiple probes in a no-signal sample. Since the no-signal sample includes no signal at all, any data in the core of the probes is due to noise of the pre-characterized platform. Accordingly, the spectral representation of the probes characterizes the noise in platform.

A general noise signature can be specified based on the no-signal probes by using those frequency components in the spectral representation that have small fluctuations from probe to probe. The general noise signature can disregard frequency components that show large probe-to-probe fluctuations. Thus the general noise signature is specific to the platform array and the detection method, and independent of the types of probes in the array.

Optionally, the general noise signature can be customized for a particular probe. The function generator 100 can specify a noise signature for a particular probe by comparing spectral representations for the probe in different reference samples and selecting the spectral components that have small fluctuation from sample to sample. The probe specific noise signature can be defined using no-signal and/or false signal samples.

The noise signature can include components that are artifacts of the pre-characterized platform, and appear in the acquired data independent of whether a signal is present or not. The function generator 100 can exclude such artifacts from the noise signature of the platform by analyzing noise in true-signal samples the same way as for no-signal or false signal samples. For example, noise can be characterized by the spectral representation of data in the core of a probe in a true-signal sample and multiple no-signal samples. By comparing the spectral representation of the true-signal sample and the no-signal samples, the function generator 100 can select components of the spectral representation that are similar in all no-signal samples but different in the true-signal sample. The selected portions can be used to define a noise signature for the probe. The function generator 100 can optimize the number of spectral components in the noise signature according to design parameters, such as limit and range of detection.

The function generator 100 calculates parameters for the canonical dynamical model based on the identified noise features (step 340). The canonical dynamical model can be used to enhance signals that are below noise level. For example, the dynamical model is designed such that it responds differently to different excitations. In particular, certain responses are smaller for excitations that corresponds to the identified noise features and larger for excitations that correspond to signals. Thus in these responses, the dynamical model enhances the signals relative to the noise level.

In one implementation, the dynamical model includes a non-linear dynamical system, such as a bistable system, and a noise reservoir coupled to the non-linear system. The noise reservoir and the coupling to the non-linear system are designed based on the noise features identified in the reference samples. Alternatively, the noise reservoir can be represented by a stochastic force coupled to the non-linear system, and parameters of the stochastic force can be designed according to the identified noise features. The dynamical model can be a conservative model, where the total energy is conserved and energy is exchanged only between the non-linear system and the noise reservoir. Or the dynamical model can be dissipative, where energy is dissipated from the system, for example, by stochastic forces. Exemplary dynamical systems are discussed with reference to FIG. 10.

The function generator 100 can match some spectral properties of the dynamical model and the noise features identified for the noise signature. For example, a non-linear dynamical system can be coupled to a noise reservoir that includes frequency components corresponding to the identified noise feature. The function generator 100 selects couplings between the noise reservoir and the non-linear system to match the spectrum of fluctuations (i.e., noise) in the non-linear system with the spectrum of the identified noise features. For example, the non-linear system's fluctuation spectrum is calculated (if analytical formulas are available) or measured in simulations (if no analytical formulas are available) for different couplings, and compared to the noise features. Based on the comparison, the couplings can be varied until a "matching criterion" is met.

In addition, the function generator 100 can set some parameters of the non-linear dynamical system using calibrated true-signal samples. To achieve desired resolution or limit of detection for signal analysis, the response of the non-linear dynamical system can be calculated for excitations corresponding to different signal levels according to the calibrated samples. The responses to the different signal levels are compared to the response when no signal is present to verify whether the desired resolution or limit of detection can be met with the dynamical model. If not, parameters of the dynamical model can be adjusted to reach an optimal resolution or limit of detection.

The function generator 100 defines an expressor function based on the dynamical model and the noise signature of the platform (step 350). The expresser function characterizes the dynamical model's response to an excitation. The dynamical model's response and its final state can be determined by interferometrically coupling the expressor function to the excitation. The expresser function can be defined based on analytical calculations, computer simulations or heuristic methods, such as trial and error. The expresser function can be an explicit function or provide parameters for an algorithm that calculates the response of the non-linear dynamical system. Example responses are discussed below with reference to FIG. 11.

FIG. 8 illustrates an exemplary data array 410 acquired from an arrayed platform (such as by scanning a biochip, etc.). An enlarged portion 420 illustrates spots 422, where each spot corresponds to a respective probe and includes multiple pixels. Exemplary acquired data and how to transform it into spectral representation. Describe the shown biochip. List other examples including different biochips and mass spectroscopy. Indicate other ways to generate spectral representation.

Figure 9:
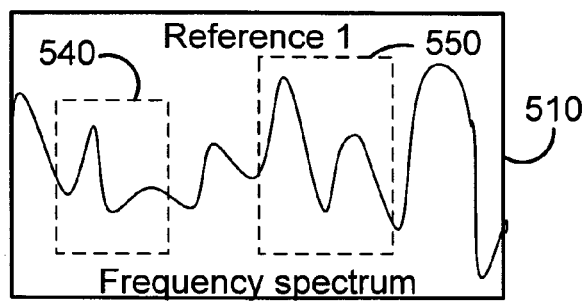
FIG. 9 is a schematic diagram illustrating noise analysis in reference samples.
Figure 9:
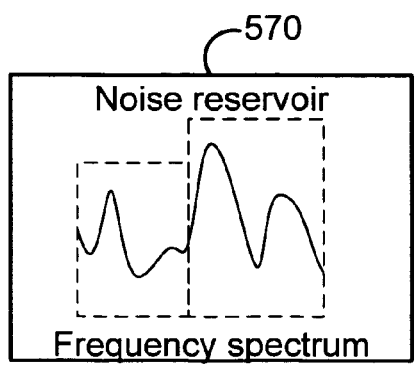
Figure 9:
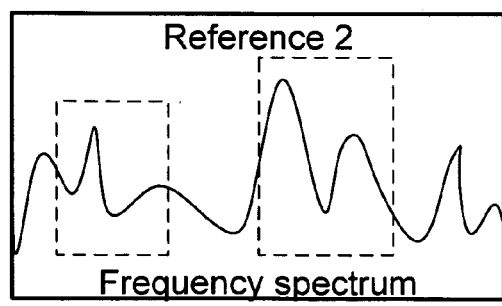
Figure 9:
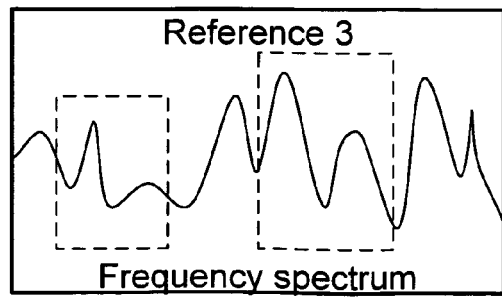

FIG. 9 illustrates various amplitude vs. frequency spectra 510, 520, 530 in which selected windows of such spectra 540, 550 may be used to generate a noise reservoir 570. In Reference 1 510, window 540 identifies a section of spectra that is sensitive to changes in concentration may be utilized to determine a sensitivity of a regions of spectra. Higher order statistical operators including bispectral and trispectral measures are computed to determine properties of the regions of the spectra.

In one variation, regions of frequency spectra that are of interest may be determined by transforming the spectra into spectral energies that can be associated with specific events of interest or classified as signal and noise. Subsequently, it may be determined which regions of frequency spectra are most representative of noise and or background and/or which spectral regions are most vulnerable to background interference so that they may be eliminated from modeling. The selected spectral regions may then be validated using calibrated non-specific data. The spectral regions that are most representative of noise may be used to generate/form the noise reservoir. Energy asymmetry between spectral energy of regions deemed to be most characteristic of signal and spectral regions most representative of noise may then be computed to initialize transition rate equations for the bistable model.

Additional calibrated examples may also be used to determine if energy asymmetry is adequate to produce observable tunneling rate when conditions of quantum stochastic resonance are met. A qualitative difference in tunneling rate must be observed when known examples of signal and no-signal incoming data are introduced in the system. Statistically significant change in tunneling rate, e.g., greater than or equal to two standard deviations over the root mean square (RMS) noise in tunneling rate when incoming data is only noise is sufficient to conclude that a qualitative difference tunneling rate is observed. A less stringent statistical criteria may be used if the magnitude of average tunneling rate is >1 for a particular data modality. If the energy asymmetry is inadequate to produce a qualitative change in observable tunneling rate between signal and noise, a synthetic resampling techniques (such as Renka Cline algorithm, convolve with wavelet kernels or convolve with other 1-D, 2D- or higher dimensional spectral kernels) may be used to generate additional spectral harmonics in the incoming data and repeat the above steps may be repeated. If a qualitative change in tunneling rate is observed then go to 234.

An example to identify noise signature and selecting frequency components for the noise reservoir entails transforming the incoming data modality into a spectral regime through Fourier transforms. The transformed data is then analyzed to determine periodicity of different spectral windows using different combinations of spectral harmonics. When spectral regions are identified with different periodicities corresponding to signal and noise examples, then these regions are used to compute spectral energies to determine the energy asymmetry for initializing the bistable system dynamics. The noise reservoir and its interaction with the dynamical system are designed to quickly absorb noise in acquired data to be analyzed.

Figure 10:
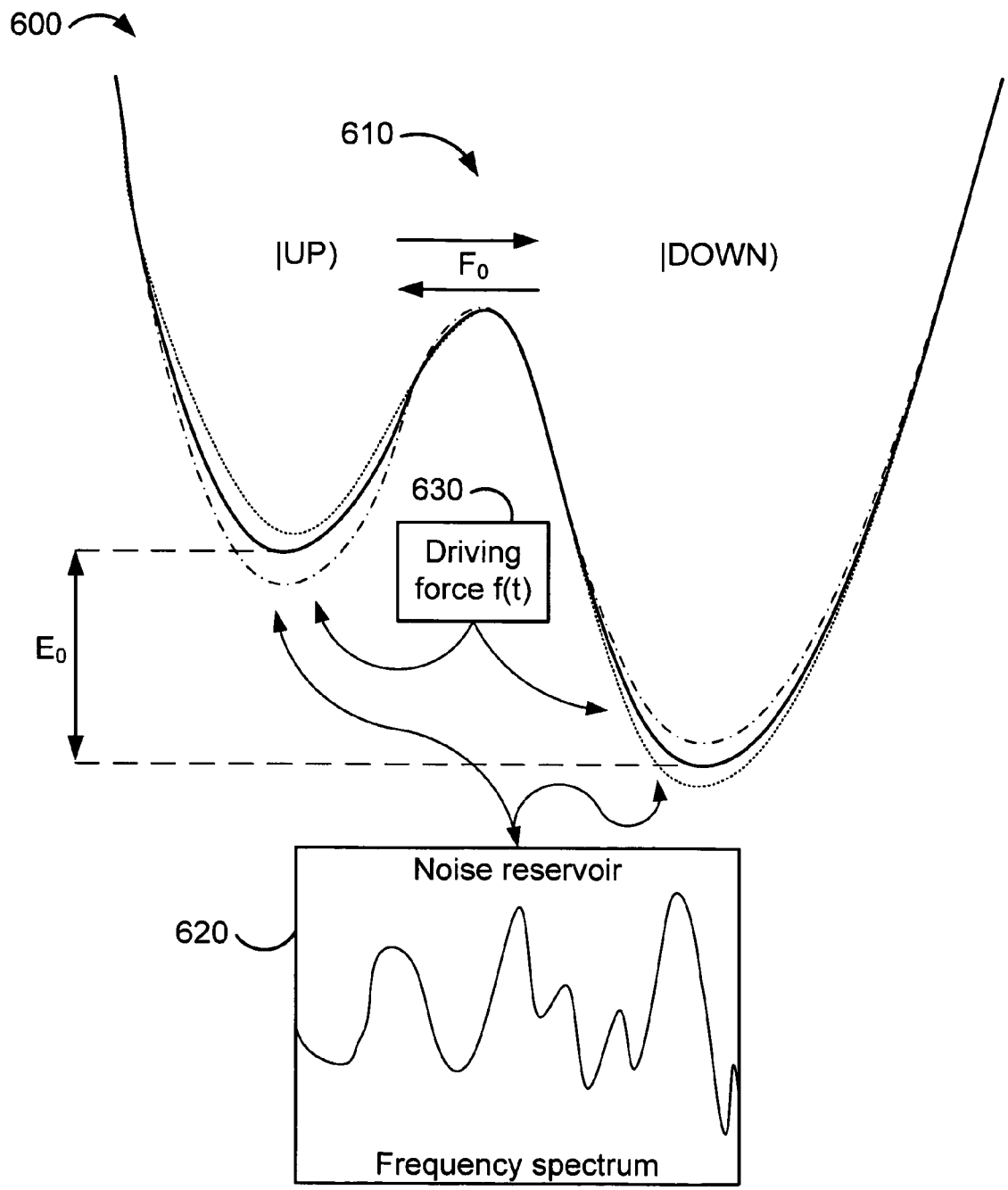
FIG. 10 is a schematic diagram illustrating a dynamical model for signal analysis.

FIG. 10 illustrates a canonical (e.g., a spin-boson quantum double system see, for example, M. Grifoni et al., "Dissipation, Decoherence and Preparation Effects in the Spin-Boson System", Eur. Phys. J. B 10, 719-729 (February 1999), etc.) dynamical model 600 that can be used to generate expressor functions for signal analysis. The dynamical model includes a two-state (bistable) system 610 and a noise reservoir 620 coupled to the two-state system 610. The two-state system 610 is also subject to a driving force 630 that can induce transitions between the two states of the system.

The two-state (bistable) system 610 has certain characteristics that show noise invariance. Excitations ("n") that are similar to the noise from the noise reservoir 620 cause negligible change to a characteristic noise ("N") in the system 610. However, if an excitation includes signal ("S") with an amplitude that is about the same or larger than a small threshold ("$\epsilon$"), the state of the system 610 and the characteristic noise N do substantially change. That is, the signal interferes with the noise. Stating this schematically according to this system:

n+N is similar to N, but $\epsilon$S+N is not similar N.

For example, the noise in the two-state system 610 can be characterized by a typical transition frequency ("$F_0$") between the two states of the system 610. If the system receives excitations including both signal, with an amplitude ("$\delta$"), and noise N, the transition frequency depends essentially only upon the signal, i.e., $F_0[\delta S+N] \rightarrow F_0[\delta S]$.

By repeatedly exciting the system 610, the signal portion $\delta S$ can be accumulated to reach the threshold level $\epsilon$, while the noise N is mostly absorbed in the noise reservoir 620. At the threshold level $\epsilon$, a resonance happens and the system 610 changes its state. In the new sate, the characteristic frequency $F_0$ starts to change its value at a different rate for the repeated excitations. The rate change allows detecting the resonance. After a number of excitations, if the rate has not changed, no signal is present; if the rate has changed, the signal is present.

The two-state system 610 is a non-linear dynamical system that has an "|UP)" state and a "|DOWN)" state separated by a barrier. The system can make transitions between the |UP) and |DOWN) states. Such transitions depend on a barrier height between the two states and the energy level in the two-state system 610. This energy level can change through energy transfer to and from the noise reservoir 620 and due to the driving force 630.

In a physical phenomenon called stochastic resonance, a periodic signal can be enhanced using a non-linear dynamical system similar to the two-state system 610. In stochastic resonance, the periodic signal is enhanced by increasing a noise level in the system. The noise can be a stochastic noise, such as Gaussian white noise. The periodic signal is included in the driving force at an amplitude that is insufficient to induce transitions through the barrier separating the two states. For noise levels that are substantially smaller than the energy barrier, essentially no transitions are induced between the two states. On the other hand, for noise levels that are substantially larger than the energy barrier, the transitions are driven entirely by the stochastic forces of the noise, independent from the periodic signal. In between, the transitions have both a stochastic component and a component that is correlated with the periodic signal. Near a resonance level of the noise, the transition component which is correlated with the signal can become larger than the stochastic component. Thus the periodic signal is enhanced relative to the noise.

Instead of a fully stochastic noise, the dynamical model 600 can use the noise reservoir 620 that has a designed frequency spectrum. The noise reservoir 620 can have a frequency spectrum that is designed to enhance signals other than periodic signals. For example, the noise reservoir 620 can have a frequency spectrum that corresponds to noise that is typical in a particular type of experiment. If the two-state system 610 is driven by a driving force that includes no signal but the typical experimental noise, the driving force just adds the same type of noise that the system 610 already receives from the noise reservoir 620. Thus the system 610 has dynamics corresponding to an increased noise level from the noise reservoir. On the other hand, if the two-state system 610 is driven by a driving force that includes both a signal and the typical noise, the signal can be enhanced by selecting a resonance level for the noise received from the noise reservoir 620. Thus near the resonance level in the system 610, the signal can induce dynamics that is qualitatively different from the dynamics corresponding to the increased noise level. The signal can be detected by characterizing the dynamics of the system 610 in response to excitations, such as driving forces.

There is a natural tendency of the dynamic model 600 to preserve equilibrium of transition rate, i.e., left to right and right to left transitions between the two minima. With such an arrangement, incoming data is transformed to a driving periodic force. If the incoming data solely comprises noise, then it cannot disturb the equilibrium. However, if incoming data contains signal (e.g., signal associated with an event of interest), it will disturb equilibrium between the two transition rates. Such disturbances in equilibrium transition rate are an indicator of signal strength as embodied in the different periodicity structure between signal and noise. If it is a large magnitude signal, it will rapidly settle in minima (computer iterations), also large signal cause high or infinite tunneling rate, small signal exhibit slow tunneling rate, or small signal can stop tunneling from occurring completely. In general high noise can increase average tunneling rate. A comparison of changes in tunneling rate between injected noise and incoming data may be determined. Thereafter, using calibrated samples, differences in tunneling rate may be determined to facilitate distinguishing signal from noise.

In one implementation, the dynamical model 600 is a quantum model in which the two-state system 610 and the noise reservoir 620 are described by half spin operators (Pauli matrices) and quantum oscillators (bosons), respectively. Quantum oscillators can have only discrete energy discrete values (i.e., they are quantized). The quantum oscillator has excitations that behave as bosons (as opposed to fermions), because multiple excitations can be in the same quantum state (while only one fermion is allowed in one quantum state).

Spin operators, in general, describe a spinning quantum object. The spin operators describe a spin vector about which the object is spinning. The spin vector has a length that depends on the rotation rate. While a classical object's spin vector can point in any direction and can have any length, a quantum object's spin vector can have a length that takes only discrete values. The shortest length is a half spin (on the scale of the Planck constant). In addition, quantum spin vectors can have only two possible directions relative to a coordinate axis: up or down.

Accordingly in the dynamical system 610, the |UP) and |DOWN) states are defined as quantum states. These quantum states define a phase space of a spin operator having an x-component $\sigma_x$, a y-component $\sigma_y$, and a z-component $\sigma_z$. The z-component $\sigma_z$ can be used to represent energy differences between the |UP) and |DOWN) states, because $\sigma_z$ has different eigenvalues for the two states, e.g., +/−1, $\sigma_z|UP)=|UP) \ \sigma_z|DOWN)=-|DOWN)$.

The x-component $\sigma_x$ induces transitions between the two states as $$\sigma_x|UP\rangle=|DOWN\rangle\ \sigma_x|DOWN\rangle=|UP\rangle.$$

Therefore, the two-state system 610 can be described using the $\sigma_z$ operator to specify an energy difference ("$E_0$") between the $|UP\rangle$ and $|DOWN\rangle$ states. The driving force 630 ("$f(t)$") can be added to modulate the energy difference. An effective barrier between the two states can be represented by the $\sigma_x$ operator whose coefficient ("D") corresponds to a transition frequency between the two states. Thus the two-state system 610 can be represented by a spin Hamiltonian ("$H_s$") as $$H_S=(E_0+f(t))\sigma_z+D\sigma_x.$$

The noise reservoir 620 can be represented by a boson Hamiltonian ("$H_B$") describing noise that is generated by multiple quantum oscillators, where each oscillator has a characteristic frequency $\omega$, and has an energy described by a corresponding boson operator ("$b_\omega>$", which decreases the oscillator's energy) and its conjugate ("$b_\omega^+$", which increases the oscillator's energy) as $$H_B=-\Sigma_\omega \omega b_\omega^+ b_\omega+\text{const}.$$

The frequency spectrum of the noise reservoir is determined by the characteristic frequencies of the quantum oscillators and the reservoir's interaction with the two-state system.

In the noise reservoir 620, each oscillator is coupled to the z-component $\sigma_z$ of the two-state system 610 with a corresponding coupling ("$K_\omega$") according to an interaction Hamiltonian ("$H_1$") as $$H_1=-\sigma_z\Sigma_\omega K_\omega(b_\omega^+ +b_\omega).$$

The interaction Hamiltonian $H_1$ describes an energy exchange between the two-state system 610 and the noise reservoir 620. For a particular frequency $\omega$, the larger the coupling $K_\omega$, the faster the energy exchange is at the particular frequency. Accordingly, the couplings $K_\omega$ determine the noise spectrum generated by the interaction Hamiltonian $H_1$ in the two-state system 610.

A full spin-boson Hamiltonian ("H") of the dynamical model 600 includes the spin ($H_S$), the boson ($H_B$) and the interaction ($H_1$) Hamiltonians as $$H=H_S+H_B+H_1.$$

If there is no driving force 630, the two-state system 610 can be in an asymmetric mixed quantum state in which the $|UP\rangle$ state has a smaller weight than the $|DOWN\rangle$ state. Between the $|UP\rangle$ and $|DOWN\rangle$ states transitions occur with some probability. These transitions have a characteristic frequency ("$F_0$") that depends on the parameters $E_0$ and D of the spin Hamiltonian and the couplings between the spin and boson Hamiltonians. These parameters and couplings can be selected such that the asymmetry of the sate and the characteristic frequency $F_0$ are essentially stable for a preselected range of a total energy in the model 600. From a statistical point of view, the range of the total energy corresponds to a temperature range.

If the two-state system receives an external excitation, such as the driving force 630, the two-state system 610 changes its asymmetric state to a new quantum state. If the driving force 630 includes a noise component that is similar to the noise received from the noise reservoir 620, the driving force 630 increases only the noise level and the temperature in the two-state system 610 without substantially altering the asymmetry of the state or the characteristic frequency $F_0$. However, if the driving force 630 includes a signal component that is different from the noise from the noise reservoir 620, the new quantum state can be substantially different from the asymmetric quantum state that corresponds to no signal. For example, the new quantum state may become more symmetric or the characteristic frequency $F_0$ may change because the signal has a weak coupling to the noise reservoir 620. The substantial change of the quantum state in response to signals is referred to as quantum resonance interference ("QRI"). Generating and detecting quantum resonance interference in two-state systems is further discussed with reference to FIGS. 7 and 8.

In alternative implementations, the dynamical model 600 can include other non-linear dynamical systems, such as quantum systems with more than two states or multiple two-state systems coupled together. Instead of quantum systems, the dynamical model 600 can include classical systems describing the two-state system 610 or the noise reservoir 620 or both. For example, the two-state system 610 can include a double-well potential ("U(x)") in which a classical particle is moving along a direction x. In addition to a force dU/dx from the potential, the classical particle is subject the driving force f(t) and a stochastic force ("N(t)") describing an interaction between the particle and the noise reservoir. The dynamics of the particle is described as $$dx/dt=dU/dx+f(t)+N(t).$$

Similar to the quantum case, a response of the classical system can be different for different excitations in the driving force f. If the driving force includes noise that is similar to the stochastic noise N, only the noise level is increased in the system. If the driving force includes a signal, the signal may be enhanced by stochastic resonance.

Figure 11:
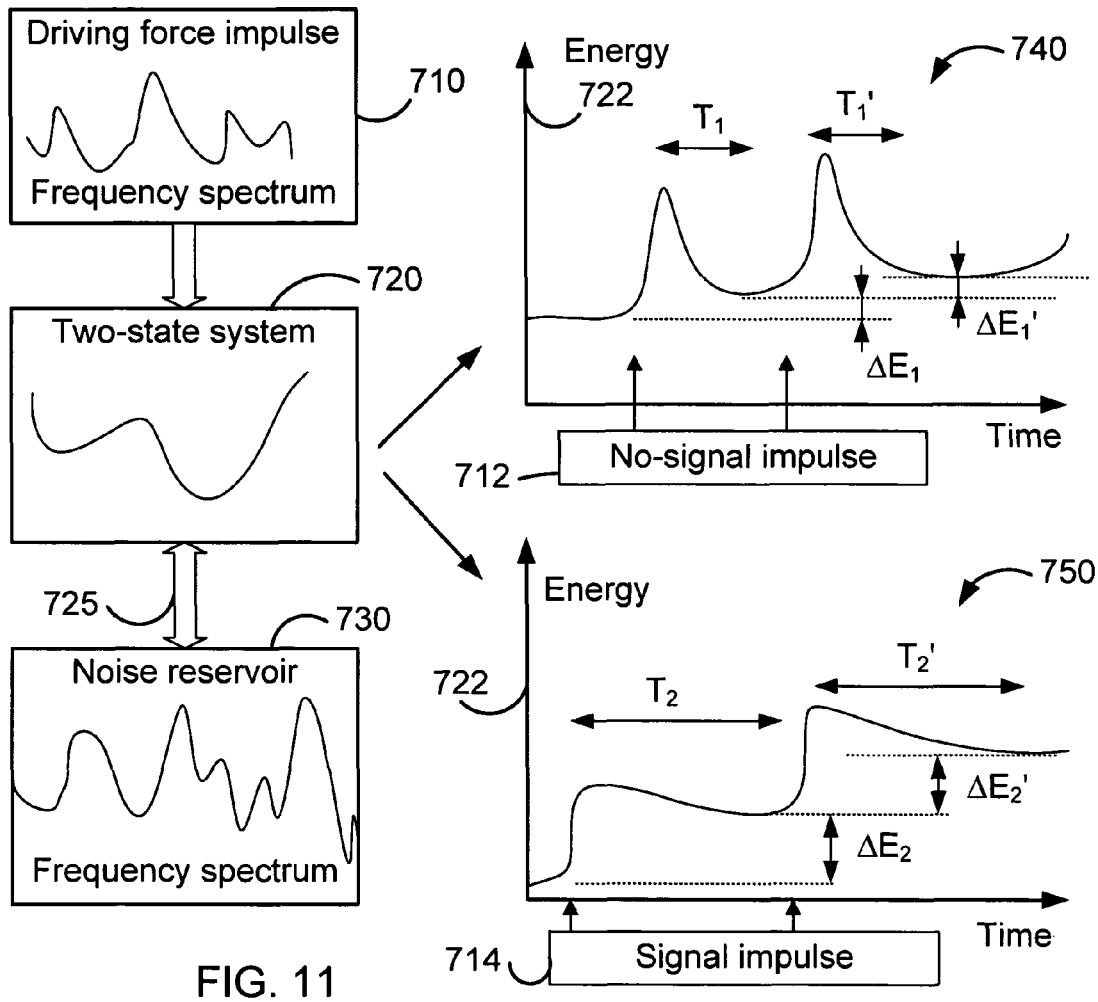
FIG. 11 is a schematic diagram illustrating measuring dynamical quantities in a driven dynamical model for signal analysis.

FIG. 11 illustrates using a driving force impulse 710 to excite a two-state system 720 that has a coupling 725 to a noise reservoir 730. The two-state system 720 is a non-linear quantum system similar to the quantum two-state system 610 discussed above with reference to FIG. 10. The noise reservoir 730 is designed to generate a noise in the two-state system through the coupling 725 such that the generated noise is similar to typical noise in the driving force impulse 710.

When the driving force impulse 710 is applied, energy is injected into the two-state system 720. The injected energy excites the two-state system 720 and raises its energy 722. As the excitation decays, the injected energy is redistributed between different degrees of freedom of the two-state system 720 and, due to the coupling 725, the noise reservoir 730. After some relaxation time, the system reaches a new state. Properties of the decay and the new state can be calculated using an expressor function, as discussed above with reference to FIGS. 6 and 7.

A schematic diagram 740 illustrates how the energy 722 of the two-state system 720 changes if a no-signal impulse 712 is applied to the two-state system 720. The no-signal impulse 712 is a driving force impulse that includes only the typical noise. As the no-signal impulse 712 is being applied, energy is injected into the two-state system 720. Because the no-signal impulse 712 has only typical noise that is similar to the noise from the noise reservoir 730, most of the injected energy is absorbed in a short relaxation time ("$T_1$") in the noise reservoir 730 through the coupling 725. After the injected energy is redistributed in a new state of the system, the energy 722 has been increased by a small amount ("$\Delta E_1$"). The energy increase $\Delta E_1$ corresponds to an increased noise level due to the injected energy. If a no-signal impulse 712 is applied in a second iteration, the two state system 720 may have different relaxation time $T_1'$ and energy increase $\Delta E_1'$ than for the first impulse due to the previous changes in the system.

A schematic diagram 750 illustrates how the energy 722 of the two-state system 720 changes if a signal impulse 714 is applied to the two-state system 720. The signal impulse 714 is a driving force impulse that includes a signal in addition to the typical noise. As for the no-signal impulse 712, energy is injected into the two-state system 720 as the signal impulse 714 is applied, and the noise reservoir 730 absorbs the portion of the injected energy that represents typical noise in a short time. For the portion of the injected energy that represents the signal, the decay takes a longer relaxation time ("$T_2$"). The injected energy is redistributed in a new state in which the energy 722 has been increased by a larger amount ("$\Delta E_2$") than in the case of no-signal impulse. (That is, less energy has been absorbed in the noise reservoir.) The energy increase $\Delta E_2$ corresponds not only to an increased noise level but also a characteristic change in the quantum state of the two-state system. If a signal impulse 714 is applied in a second iteration, the two state system 720 may have a different relaxation time $T_2'$ and energy increase $\Delta E_2'$ than for the first impulse due to the previous changes in the system.

The signal can be detected by comparing the system's responses to the signal impulse 714 and the no-signal impulse 712. For example, the no-signal impulse 712 can be generated by a system similar to the noise reservoir 730. The system's response can be characterized by a dynamical quantity ("Q(k)") that is defined for a k-th iteration by a difference between the energy increase $\Delta E_1(k)$ at the k-th application of a no-signal impulse 712 and the energy increase $\Delta E_2(k)$ at the k-th application of a signal impulse 714 as $$Q(k) = \Delta E_2(k) - \Delta E_1(k).$$

Alternatively, the system's response can be characterized by the relaxation time T or any other dynamical quantity that is different if a signal is present.

Figure 12:
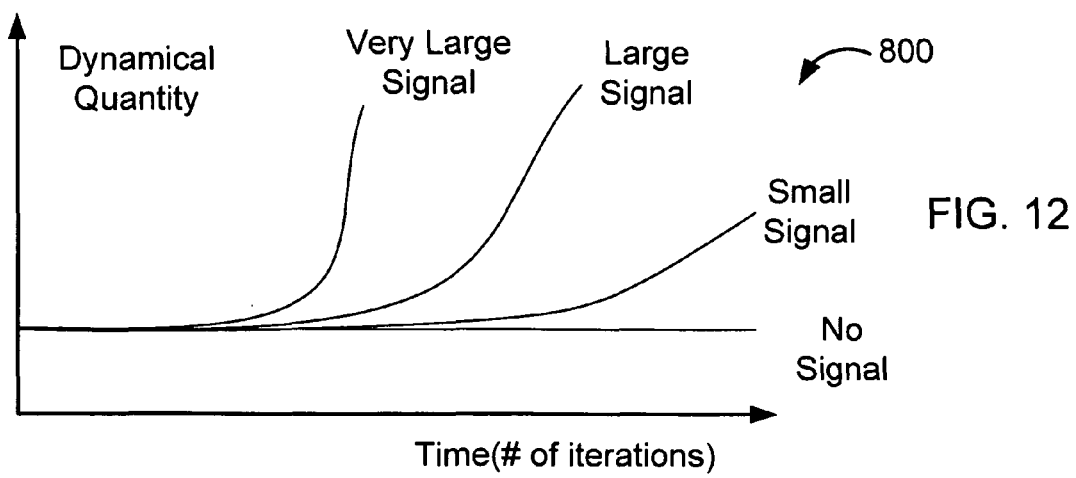
FIG. 12 is a schematic diagram illustrating time dependence of a dynamical quantity in a driven dynamical model for signal analysis.

FIG. 12 is a schematic diagram 800 illustrating how a dynamical quantity ("Q") changes when excitations are applied to a non-linear dynamical system coupled to a noise bath that is designed according to a typical noise in the excitations. For example, the dynamical quantity can be based on comparing the energy increase in a two-state quantum system in response to no-signal impulses and sample impulses that may or may not include a signal, as discussed above with reference to FIG. 11. The excitations, such as driving forces, can be applied continuously or iteratively in impulses.

The presence of the signal can be detected by analyzing the functional form of the dynamical quantity Q as a function of the number of iterations (or time for continuously applied driving forces). If no signal is present in the iteratively applied sample impulses, the two-state system responds substantially the same way to the sample impulse than the no-signal impulse even as the number of iterations is increasing. Accordingly, the dynamical quantity Q is represented by flat curve as a function of iterations/time.

If a small signal is present in the iteratively applied sample impulses, the two-state system responds slightly different to the sample impulse than the no-signal impulse. However, the quantum state of the two-state system is also changed due to the presence of the signal. The change of the quantum states couples back to the response of the system, which becomes more and more different from the no-signal case as the number of iterations is increasing. Due to the feedback mechanism, the dynamical quantity Q departs in a non-linear way from the flat curve of the no-signal case at a critical number of iterations. As the signal's level is increasing relative to the noise in the sample impulses, the critical number of iterations is decreasing.

Figure 13:
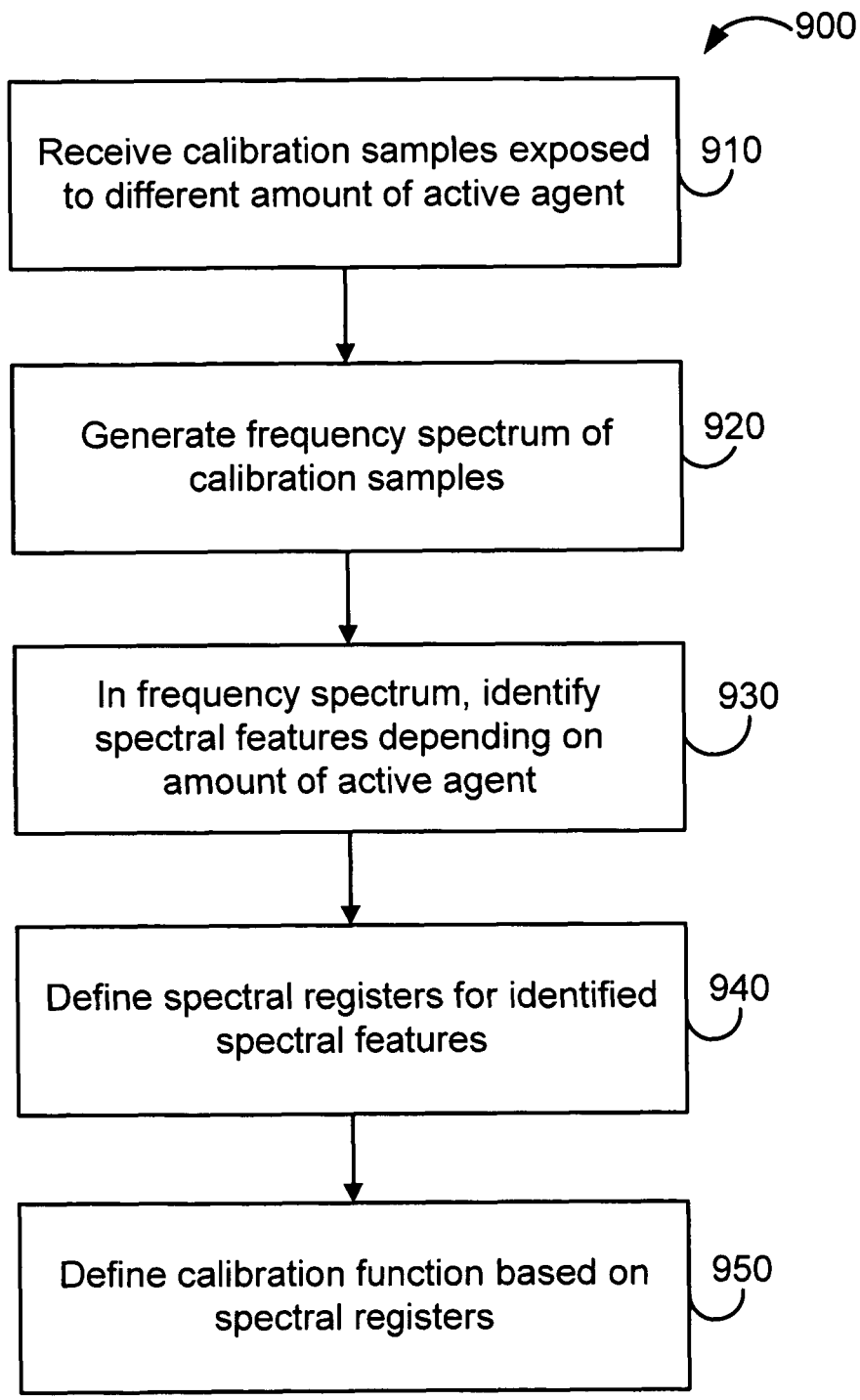

FIG. 13. illustrates a method 900 for defining calibration functions using spectral registers. The defined calibration functions can be used to quantitate signals measured in an pre-characterized platform. The method 900 can be performed by a function generator 100, such as the function generator 100 (FIG. 5) that includes a response calibrator.

The function generator 100 receives calibration samples (step 910). Each calibration sample corresponds to a particular level of active agent measured in the pre-characterized platform. For example, the calibration samples can include microarrays exposed to a controlled amount of a particular gene whose hybridization complement is included in one or more probes in the microarray. The calibration samples can be prepared by diluting a first biological sample including a first concentration of a gene. A second calibration sample with half of the first concentration can be prepared by diluting the first sample according to a dilution ratio of two. A third calibration sample can be prepared by further diluting the second sample according to the same or a different dilution ratio. Further samples can be prepared by further dilutions.

The function generator 100 generates a frequency spectrum of the calibration samples (step 920). For each calibration sample, the function generator 100 identifies probes that measure the active agent, preprocesses and serializes the acquired data points corresponding to the identified probes, and Fourier transforms the serialized data to generate the frequency spectrum of the calibration sample. The frequency spectrum can be based on the amplitude or the phase of the Fourier transform.

The function generator 100 can generate the frequency spectrum using a noise analyzer, such as the noise analyzer 232 (FIG. 6), that is also used to identify noise signature of the pre-characterized platform. Alternatively, the function generator 100 can use a frequency spectrum generator that uses different preprocessing, serialization or frequency transformation technique than the noise analyzer. For example, the frequency spectrum generator can use different filters to preprocess the data. Or instead of using a one-dimensional Fourier transform, a two-dimensional Fourier transformation can be applied without serializing the data.

In the generated frequency spectrum, the function generator 100 identifies spectral features that depend on the concentration of the active agent in the calibration samples (step 930). In one implementation, the function generator 100 identifies spectral features in the noise signature of the pre-characterized platform. Alternatively, the function generator 100 can identify spectral features in the entire frequency spectrum.

Figure 14:
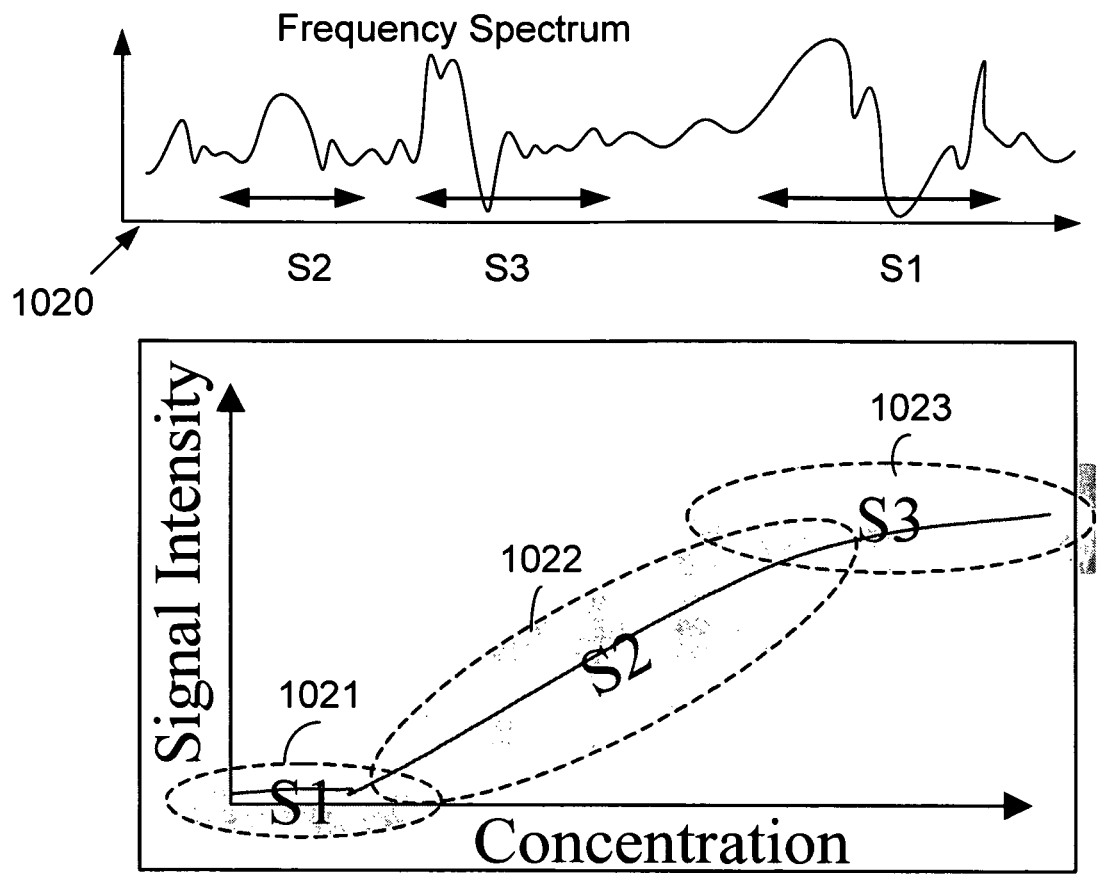
FIG. 14 is a schematic diagram illustrating spectral registers for quantitating detected signals.

The function generator 100 also identifies concentration ranges corresponding to the identified spectral features. Each identified feature depends on the concentration of the active agent in the corresponding range. The function generator 100 can identify different spectral features for different concentration ranges. For example, a first spectral feature can emerge as the concentration of the active agent increases between zero and a first concentration but disappear for larger concentrations. Above the first concentration, a second feature can emerge at another frequencies of the spectrum. The function generator 100 identifies the first and the second features, and associates the first feature with concentrations between zero and the first concentration, and the second feature with concentrations larger than the first concentration. An exemplary implementation of identifying spectral features is illustrated in FIG. 14.

The function generator 100 defines a spectral register for each identified spectral feature (step 940). Each spectral register identifies frequency components that contribute to the corresponding feature. The spectral register is associated with the same range of concentrations as the corresponding feature. Different spectral registers can overlap, that is, the same frequency component can contribute to more than one spectral register.

The spectral register can also specify conditions to determine whether the spectral feature is present or not in the register. For example, each spectral register can specify a spectral weight to characterize the corresponding spectral feature, and a range of the spectral weight for which the feature is present. The spectral weight can be calculated from the frequency components specified by the register. For example, the spectral weight can be calculated by applying a filter corresponding to the feature.

The function generator 100 defines a calibration function based on the spectral registers (step 950). For each spectral register, the response calibrator 238 defines a corresponding functional component that is used if the spectral register is selected. The functional component describes the functional relation within the concentration range of the register between the concentration of the active agent and an enhanced signal strength, such as a resonance amplitude. The resonance amplitude characterizes how fast a signal is enhanced according to a predetermined criterion by an active signal analysis, such as quantum resonant interference. For example, the predetermined criterion can be based on a preset signal level, and the resonance amplitude can be inversely proportional to the number of successive signal enhancing steps applied to the original signal to reach the preset signal level. Accordingly, a small resonance amplitude corresponds to a weak signal that is enhanced in many steps and a large resonance amplitude corresponds to a strong signal that is enhanced in a few steps.

Typically, there is a non-uniform relation between the concentration of the active agent and the resonance amplitude. For increasing concentration of the active agent, the resonance amplitude changes slower at small and large concentrations than in between. The spectral registers can be defined to linearize the relation between the measured signal strength and the concentration of the active agent. For example, spectral registers can be defined to match quasi-linear portions of the relation between the concentration and the resonance amplitude.

FIG. 14 illustrates spectral registers defined for quantitating a signal intensity. In the example, three spectral registers ("S1", "S2" and "S3") are defined. These registers correspond to three qualitative "quantitation performance" regimes observed in passive signal processing systems. S1 corresponds to the regime where signal is weaker than background and the incoming data amplitude is dominated by noise. In this regime, signal is buried below noise and difficult to accurately quantitate. S2 corresponds to the linear regime where signal is above background noise and signal value associated with events of interest can be quantitated with high accuracy based on detected intensity values. S3 corresponds to the regime where signal is extremely high and detector suffers from saturation effects.

Within the framework of QRI, signal quantitation may be determined via a reformulation to a nonlinear detection problem. The following method may be applied.

The overall dynamic range of interest is partitioned into the three qualitative regimes S1, S2, and S3

Cutoff-boundaries for S1, S2 and S3 are established using error norm analysis. For example, in medical diagnostic applications, a fall-off of coefficient of variation expressed as a percent (% CV) or a specific percent change in the linearity (measured via coefficient of regression—$R^2$)

S1, S2, and S3 registers are associated with quantitation levels of interest. For example the RNA transcript quantitation level in a microarray based diagnostic application, partitioned into S1 [<0.5 pM] concentration, S2 [0.5, 128 pM] concentration and S3 [>128 pM] concentration.

S1, S2 and S3 registers are further partitioned into subregisters based on desired precision of interest. For example, a 20% fold change precision detection application partitioning S1 between 0.01 pM and 0.5 pM partitioned into discretized 250 subregisters.

Expressor function yielding S1, S2, and S3 as an additional output in addition to enhanced data or signal detection.

The expressor function iterations are calibrated to match the detection to a specific subregister. For example, signal presence in the S1 regime, if detected in a single QEF application would correspond to 0.5 pM concentration. If detected in $2^{nd}$ iteration the concentration would correspond to 0.48 pM, and so on.

The energy asymmetry is computed and modified to match the desired quantitation precision. Observable tunneling rate changes may be used to distinguish signal and noise are a function of the energy asymmetry in the optimization and selection of the parameters for the bistable system. Therefore, energy asymmetry may act as a controlling variable for addressing a desired limit of detections quantitation, etc. Also, energy asymmetry may be used to tune the sensitivity of the expressor function and coupler.

Each spectral register specifies a spectral region in a frequency spectrum 1010 of data acquired from a probe that hybridizes with an active agent in a biological sample. The frequency spectrum 1010 can be calculated from the acquired data by serializing the acquired data and applying a Fourier transformation to the serialized data.

Each spectral register corresponds to a concentration range of the active agent. For example, the first spectral register S1 can correspond to a range from zero to 2 pM, the second spectral register S2 can correspond to a range from 1 to 100 pM, and the third spectral register S3 can correspond to a range from 80 to 200 pM. If the sample includes a concentration of the active agent within the range corresponding to a register, a spectral feature is present in the spectral region of the spectral register.

FIG. 14 also illustrates a function 1020 describing a relation between a concentration of the active agent and a signal intensity generated by active signal processing. The function 1020 has a first 1021, a second 1022, and a third 1023 functional component, corresponding to the registers S1, S2 and S3, respectively. Each of the functional components 1012-1023 specifies a quasi-linear relationship between the signal strength and the concentration of the active agent. In the first 1021 and third 1023 functional components, the signal strength is a slowly varying function of the concentration. In the second functional component 1022, the signal strength varies more quickly with the concentration.

By detecting which of the spectral features is present in the corresponding spectral regions, a sample can be classified into one of the registers S1, S2 and S3. For each register, the presence of a spectral feature can be detected based on a spectral weight calculated in the corresponding spectral region, and one of the registers can be selected based on the spectral weights according to some predetermined rules.

Once a register is selected, the functional component of the register can be used to quantitate the sample's signal strength.

Figure 15:
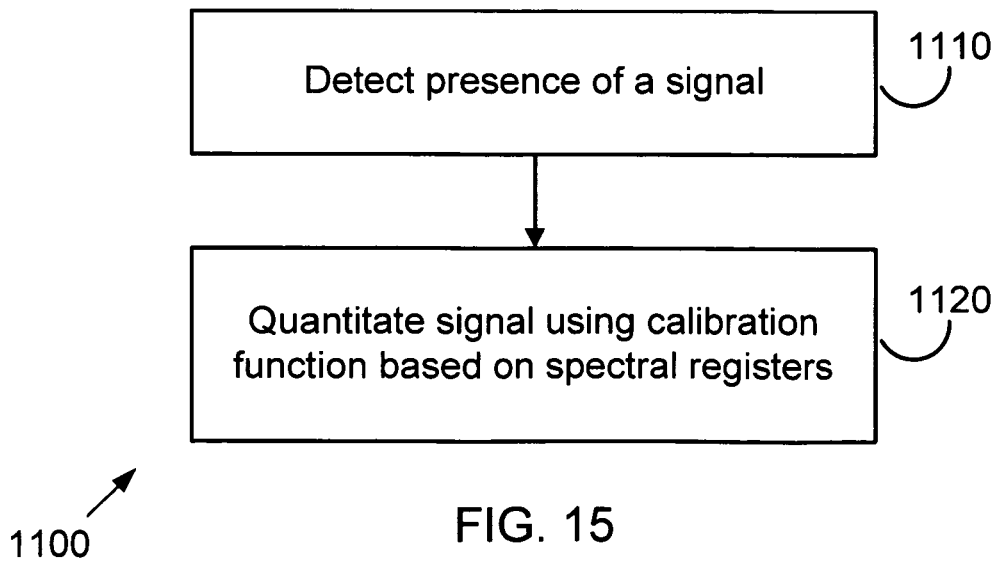

FIG. 15 illustrates a method 1100 for quantitating a signal using spectral registers. The signal is enhanced by active signal analysis, and corresponds to an active agent in a sample. The quantitated signal gives an estimate of the amount of the active agent in the sample. The method can be performed by a resonance detector and a quantitator, such as the resonance detector 108 and the quantitator 110, respectively, that receive resonance data generated by active signal analysis.

The resonance detector, at 1110, detects presence of a signal in the received resonance data. The signal can be detected by identifying a characteristic change in a dynamical quantity, as discussed above with reference to FIG. 12.

If a signal is detected, the quantitator, at 1120, estimates the amount of active agent represented by the signal using a calibration function based on spectral registers. If no signal is detected, the quantitator sets zero for the quantity of the active agent.

The calibration function uses a strength, such as a resonance amplitude, of the detected signal, and a frequency spectrum of the probe that measures the active agent in the sample. The calibration function includes multiple functional components for estimating concentration of the active agent as a function of the signal strength. Each functional component is associated with a spectral register. The frequency spectrum is used to select one of the spectral registers by detecting spectral features that correspond to a concentration range of the active agent in the sample. Based on the detected spectral features, one of the spectral registers is selected and the corresponding functional component is used to quantitate the detected signal.

The following provides an illustrative technique for developing a quantum expresser function for a microarray, such as a GeneChip produced by Affymetrix:

Preset limit of Detection (desired LOD)
Preset detection precision (units in terms of k-LOD) (note: this step is only for tracking a specific biomarker and not a general step for gene expression analysis)
Conduct empirical experiments to prepare dataset for developing QEF
  Replicate Empty hybridizations (no genomic content)
  Replicate Non-specific hybridizations
  Replicate complex background hybridizations with a low concentration spike-in (5× to 10× below desired LOD)
Conduct empirical experiments to prepare dataset to calibrate Resonance Amplitude (RA) output from a QEF The following provides an overview of a technique for applying a quantum expresser function:

Use DAT files as a starting basis
For all genes on a microarray to be analyzed:
  Use CDF library files and PSI annotation files to extract all features corresponding to particular Gene
  For all probe features:
    Use Core extraction algorithm to extract all the pixels associated with the PM and MM cells from a DAT file. Optimal core size is determined during QEF development step
    Use column-major or row-major transform coupled with a 1-D discrete Fourier transform to turn spatial intensities into spatial frequencies; or use 2-D Fourier transform to turn spatial intensities into spatial frequencies. Process to consistent with the step used to develop QEF. Denote as spectral feature vector.
    (Optional if conducting ultra-sensitive analysis) Apply computational resampling to turn an n×m pixel core into a k2.n×k2.m pixel core. Apply Fourier Transform to re-sampled core to generate additional spatial frequencies.
Precondition incoming data by Property Linking Convolution
  Convolve spectral feature vector (produced in Step 3) with 2-D canonical spectral kernel (CSK) library with specific properties.
  CSK library produced in the QEF development step. Each CSK embodies spectral properties for a 1-D state variable of an underlying bistable system exhibiting quantum stochastic resonance; using digital simulation of a 1D Spin-Boson system with known properties and known to exhibit QSR to select the CSK library kernels
  This action is performed for both PM and MM feature cells to produce preconditioned incoming spectral data
  Convolution kernel depth of 7 used for Affymetrix GeneChip arrays. This has been found to be empirically sufficient to provide robust feature LOD to 0.25 pM/ul. Depth can be varied to reach higher sensitivity.
  Preconditioned PM and MM features now embody properties of a ID bistable system exhibiting QSR if and only if the starting spatial frequencies did not embody any signal above LOD.
Apply QRI Coupler Logic
  Use passive logic on spectrally transformed feature data to determine if signal is present (sufficient for PM cells with S>B) at the feature level. Passive logic are matched filtering correlation rules using power spectral density values, Parseval Number and k-spectral components. Passive model developed using same data used in generating QEF
  If Feature level Presence Call can be made using passive logic, i.e., S>>B, then feature level RA is a measure correlated to spatial intensity 0
  If a Feature Level Present call cannot be made using Passive Logic (i.e., S≦B or S is slightly >B) then apply QEF to Preconditioned Feature to generate Feature Level RA.
    Feature Level RA is now a measure of "background disturbance"; assuming a model of pure background
    RA=0, implies that a disturbance cannot be detected above preset LOD.
  If Feature level presence is detected by QEF application, then additional logic is applied to validated that background disturbance is not an artifact. (application of Active Logic as a post-QEF step to validate feature level call.
  Aggregate Feature level calls and Feature Level RA to produce a Gene Level Call.

Various implementations of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and may be implemented in a high-level procedural and/or object-oriented programming language, and/or in assembly/machine language. As used herein, the term "information carrier" comprises a "machine-readable medium" that includes any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal, as well as a propagated machine-readable signal. The term "machine-readable signal" refers to any signal used to provide machine instructions and/or data to a programmable processor.

To provide for interaction with a user, the subject matter described herein may be implemented on a computer having a display device (e.g., a CRT (cathode ray tube) or LCD (liquid crystal display) monitor) for displaying information to the user and a keyboard and a pointing device (e.g., a mouse or a trackball) by which the user may provide input to the computer. Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server arises by virtue of computer programs running on the respective computers and having a client-server relationship to each other.

Although a few variations have been described in detail above, other modifications are possible. For example, the logic flow depicted in the accompanying figures and described herein do not require the particular order shown, or sequential order, to achieve desirable results. In addition, the current subject matter may be applied to any form of data in which there are signals that may be obscured by noise. Other embodiments may be within the scope of the following claims.

What is claimed is:

1. A method to determine a presence of a signal of interest from among sample signals, the method comprising:
   receiving, by a computer, reference data that characterizes physical samples from which sample signals including a signal of interest are obtained;
   generating, by the computer, a measurement probe based on the reference data and based on a dynamical system that responds to excitations that are correlated with the sample signals, wherein the measurement probe is configured to enhance the signal of interest in the sample signals;
   injecting, by the computer, the measurement probe into a quantum mechanical system configured to receive the sample signals including the signal of interest, to convert the sample signals from a spatial domain into a spectral domain, and to enhance the signal of interest in the spectral domain due to the measurement probe the injecting comprising repeatedly injecting the measurement probe into the quantum mechanical system for a number of iterations required to collapse the quantum mechanical system;
   determining, by the computer, whether the injection of the measurement probe into the quantum mechanical system results in a collapse of the quantum mechanical system; and
   determining, by the computer, a presence of the signal of interest within the sample signals if the quantum mechanical system collapses.

2. A method as in claim 1, wherein generating the measurement probe based on the reference data further comprises:
   analyzing fluctuations in the reference data using a spectral representation to identify a region for the measurement probe that corresponds to the signal of interest;
   serializing the sample signals according to a predetermined scheme; and
   transforming the serialized sample signals to generate a frequency spectrum of the measurement probe.

3. A method as in claim 1, further comprising associating the number of iterations with a signal magnitude.

4. A method as in claim 1, further comprising:
   obtaining multiple reference output data samples having known quantitative measurements over a range of detected intensities;
   identifying a plurality of regions across the reference data in which the quantitative measurement varies with detected intensities in a quasi-linear fashion;
   modeling each of the regions to associate the quantitative measurement with detected magnitude; and
   associating, for the sample signals, each of the detected intensities with a region and determining the quantitative measurement using the model for the associated region.

5. A method to determine a presence of a signal of interest from among sample signals, the method comprising:
   receiving, by one of more computers, a measurement probe generated based on reference data that characterizes physical samples from which sample signals including a signal of interest are obtained, the measurement probe also based on a dynamical system that responds to excitations that are correlated with the sample signals, wherein the measurement probe is configured to enhance the signal of interest in the sample signals, wherein the measurement probe is represented as a frequency spectrum;
   receiving, by the one or more computers, the sample signals including the signal of interest;
   generating, by the one or more computers, a frequency spectrum representing the sample signals;
   causing, by the one or more computers, interference between the frequency spectrum representing the sample signals and the frequency spectrum representing the measurement probe the causing comprising injecting the measurement probe via the frequency spectrum representing the measurement probe until convergence of the interference for the dynamical system; and determining, by the one or more computers, a presence of the signal of interest within the sample signals based on a convergence of the interference.

6. A method as in claim 5, further comprising:

determining a magnitude of the signal of interest based on an amount of time between the injection of the measurement probe and the convergence.

7. A non-transitory computer-readable medium tangibly embodying computer program instructions executable to cause a programmable processor to perform operations including:

receiving reference data that characterizes physical samples from which sample signals including a signal of interest are obtained;

generating a measurement probe based on the reference data and based on a dynamical system that responds to excitations that are correlated with the sample signals, wherein the measurement probe is configured to enhance the signal of interest in the sample signals;

injecting the measurement probe into a quantum mechanical system configured to receive the sample signals including the signal of interest, to convert the sample signals from a spatial domain into a spectral domain, and to enhance the signal of interest in the spectral domain due to the measurement probe the injecting comprising repeatedly injecting the measurement probe into the quantum mechanical system for a number of iterations required to collapse the quantum mechanical system;

determining whether the injection of the measurement probe into the quantum mechanical system results in a collapse of the quantum mechanical system; and determining a presence of the signal of interest within the sample signals if the quantum mechanical system collapses.

8. The medium of claim 7, wherein generating the measurement probe based on the reference data further comprises:

analyzing fluctuations in the reference data using a spectral representation to identify a region for the measurement probe that corresponds to the signal of interest;

serializing the sample signals according to a predetermined scheme; and transforming the serialized sample signals to generate a frequency spectrum of the measurement probe.

9. The medium of claim 7, the operations further comprising associating the number of iterations with a signal magnitude.

10. The medium of claim 7, the operations further comprising:

obtaining multiple reference output data samples having known quantitative measurements over a range of detected intensities;

identifying a plurality of regions across the reference data in which the quantitative measurement varies with detected intensities in a quasi-linear fashion;

modeling each of the regions to associate the quantitative measurement with detected magnitude; and associating, for the sample signals, each of the detected intensities with a region and determining the quantitative measurement using the model for the associated region.

11. A system comprising:

a programmable processor; and a computer-readable medium tangibly embodying computer program instructions executable to cause the programmable processor to perform operations including:

receiving a measurement probe generated based on reference data that characterizes physical samples from which sample signals including a signal of interest are obtained, the measurement probe also based on a dynamical system that responds to excitations that are correlated with the sample signals, wherein the measurement probe is configured to enhance the signal of interest in the sample signals, wherein the measurement probe is represented as a frequency spectrum;

receiving the sample signals including the signal of interest;

generating a frequency spectrum representing the sample signals;

causing interference between the frequency spectrum representing the sample signals and the frequency spectrum representing the measurement probe the causing comprising injecting the measurement probe via the frequency spectrum representing the measurement probe until convergence of the interference for the dynamical system; and determining a presence of the signal of interest within the sample signals based on a convergence of the interference.

12. The system of claim 11, the operations further comprising:

determining a magnitude of the signal of interest based on an amount of time between the injection of the measurement probe and the convergence.

13. A system comprising:

a programmable processor; and a computer-readable medium tangibly embodying computer program instructions executable to cause the programmable processor to perform operations including:

receiving reference data that characterizes physical samples from which sample signals including a signal of interest are obtained;

generating a measurement probe based on the reference data and based on a dynamical system that responds to excitations that are correlated with the sample signals, wherein the measurement probe is configured to enhance the signal of interest in the sample signals;

injecting the measurement probe into a quantum mechanical system configured to receive the sample signals including the signal of interest, to convert the sample signals from a spatial domain into a spectral domain, and to enhance the signal of interest in the spectral domain due to the measurement probe the injecting comprising repeatedly injecting the measurement probe into the quantum mechanical system for a number of iterations required to collapse the quantum mechanical system;

determining whether the injection of the measurement probe into the quantum mechanical system results in a collapse of the quantum mechanical system; and determining a presence of the signal of interest within the sample signals if the quantum mechanical system collapses.

14. The system of claim 13, wherein generating the measurement probe based on the reference data further comprises:
- analyzing fluctuations in the reference data using a spectral representation to identify a region for the measurement probe that corresponds to the signal of interest;
- serializing the sample signals according to a predetermined scheme; and
- transforming the serialized sample signals to generate a frequency spectrum of the measurement probe.

15. The system of claim 13, the operations further comprising associating the number of iterations with a signal magnitude.

16. The system of claim 13, the operations further comprising:
- obtaining multiple reference output data samples having known quantitative measurements over a range of detected intensities;
- identifying a plurality of regions across the reference data in which the quantitative measurement varies with detected intensities in a quasi-linear fashion;
- modeling each of the regions to associate the quantitative measurement with detected magnitude; and
- associating, for the sample signals, each of the detected intensities with a region and determining the quantitative measurement using the model for the associated region.

* * * * *

UNITED STATES PATENT AND TRADEMARK OFFICE
CERTIFICATE OF CORRECTION

PATENT NO.      : 8,484,000 B2
APPLICATION NO. : 11/219521
DATED           : July 9, 2013
INVENTOR(S)     : Sandeep Gulati It is certified that error appears in the above-identified patent and that said Letters Patent is hereby corrected as shown below:

In the Specifications

Column 1, line 17, delete "3d" and insert --3rd-- therefor.

Column 2, line 20, delete "Interometric" and insert --Interferometric-- therefor.

In the Claims

Column 30, line 9 (claim 1), delete "probe the" and insert --probe, the-- therefor.

Column 30, line 66 (claim 5), delete "probe the" and insert --probe, the-- therefor.

Column 31, line 28 (claim 7), delete "probe the" and insert --probe, the-- therefor.

Column 32, line 23 (claim 11), delete "probe the" and insert --probe, the-- therefor.

Column 32, line 57 (claim 13), delete "probe the" and insert --probe, the-- therefor.

Signed and Sealed this
First Day of October, 2013

Teresa Stanek Rea
*Deputy Director of the United States Patent and Trademark Office*